(12) United States Patent
Schaeffer et al.

(10) Patent No.: US 8,784,602 B2
(45) Date of Patent: Jul. 22, 2014

(54) BALLOON CATHETER FOR DELIVERING A THERAPEUTIC AGENT

(75) Inventors: Darin G. Schaeffer, Bloomington, IN (US); David Christian Lentz, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/477,774

(22) Filed: May 22, 2012

(65) Prior Publication Data

US 2013/0053769 A1 Feb. 28, 2013

Related U.S. Application Data

(63) Continuation of application No. 12/676,786, filed as application No. PCT/US2008/075970 on Sep. 11, 2008, now Pat. No. 8,182,446.

(60) Provisional application No. 60/971,802, filed on Sep. 12, 2007.

(51) Int. Cl.
*A61M 25/00* (2006.01)

(52) U.S. Cl.
USPC ..... 156/294; 156/293; 156/303.1; 604/96.01; 604/97.01; 604/101.02; 604/101.03; 604/101.05; 604/102.01; 604/102.02; 604/102.03; 604/103.01; 604/103.02; 604/103.11; 604/912; 604/915; 604/917; 604/919; 604/528; 606/108; 606/191; 606/192; 606/193; 606/194; 600/435

(58) Field of Classification Search
CPC ............ A61M 25/00; A61M 25/0021; A61M 25/0023; A61M 25/0026; A61M 29/00; A61M 31/00
USPC ..................................... 156/293, 294, 606.1; 604/101.02–101.03, 101.05, 604/102.01–102.03, 103.01–103.02, 604/103.11, 912, 915, 917, 919, 528; 606/108, 191–194
See application file for complete search history.

(56) References Cited

U.S. PATENT DOCUMENTS 4,571,240 A 2/1986 Samson et al.
4,744,366 A 5/1988 Jang
(Continued)

FOREIGN PATENT DOCUMENTS

DE 4225553 C1 5/1994
EP 1230944 A2 1/2002
(Continued)

OTHER PUBLICATIONS

Dorado™ PTA Dilation Catheter Brochure, Bard Peripheral Vascular, 2007, 4 pgs.
(Continued)

*Primary Examiner* — Jeff Aftergut
*Assistant Examiner* — Jaeyun Lee
(74) *Attorney, Agent, or Firm* — Brinks Gilson & Lione

(57) ABSTRACT

Catheter balloon assemblies (10) for delivering a therapeutic agent to a body vessel are provided, as well as related methods of manufacturing and methods of treatment. The catheter balloon assemblies may include a concentrically disposed dual balloon assembly at the distal portion of the catheter having an inner balloon (44), a porous outer balloon (42) concentrically arrayed around the inner balloon and a catheter shaft (30) adapted to deliver a therapeutic agent to the body vessel through the apertures in the outer balloon. Radial outward expansion of the inner balloon may urge the outer balloon into contact with the wall of a body vessel, where the therapeutic agent may be delivered from the catheter shaft through apertures in the outer balloon directly to the wall of the body vessel. Preferably, the catheter balloon assemblies include a stiffening' member (210) within the proximal portion and/or a plurality of lumens lined with a fluorinated hydrocarbon to independently inflate the inner balloon, deliver the therapeutic agent through the outer balloon and house a wire guide (50). The catheter balloon assemblies may provide improved tractability and/or pushability characteristics.

20 Claims, 12 Drawing Sheets

(56) References Cited

U.S. PATENT DOCUMENTS

| | | |
|---|---|---|
| 4,748,982 A | 6/1988 | Horzewski et al. |
| 4,777,951 A | 10/1988 | Cribier et al. |
| 4,994,033 A | 2/1991 | Schockey et al. |
| 5,049,132 A | 9/1991 | Shaffer et al. |
| 5,098,381 A | 3/1992 | Schneider |
| 5,112,305 A | 5/1992 | Barath et al. |
| 5,213,576 A | 5/1993 | Abiuso et al. |
| 5,232,444 A | 8/1993 | Just et al. |
| 5,232,445 A | 8/1993 | Bonzel |
| 5,236,413 A | 8/1993 | Feiring |
| 5,261,879 A | 11/1993 | Brill |
| 5,273,536 A | 12/1993 | Savas |
| 5,295,962 A | 3/1994 | Crocker et al. |
| 5,300,085 A | 4/1994 | Yock |
| 5,304,135 A | 4/1994 | Shonk |
| 5,318,531 A | 6/1994 | Leone |
| 5,334,147 A | 8/1994 | Johnson |
| 5,338,298 A | 8/1994 | McIntyre |
| 5,342,305 A | 8/1994 | Shonk |
| 5,380,304 A | 1/1995 | Parker |
| 5,447,497 A | 9/1995 | Sogard et al. |
| 5,458,568 A | 10/1995 | Racchini et al. |
| 5,536,252 A | 7/1996 | Imran et al. |
| 5,547,472 A | 8/1996 | Onishi et al. |
| 5,558,642 A | 9/1996 | Schweich, Jr. |
| 5,569,184 A | 10/1996 | Crocker et al. |
| 5,571,089 A | 11/1996 | Crocker |
| 5,611,775 A | 3/1997 | Machold et al. |
| 5,645,789 A | 7/1997 | Roucher, Jr. |
| 5,649,909 A | 7/1997 | Cornelius |
| 5,669,874 A | 9/1997 | Feiring |
| 5,685,847 A | 11/1997 | Barry |
| 5,704,913 A | 1/1998 | Abele et al. |
| 5,730,733 A | 3/1998 | Mortier et al. |
| 5,755,685 A | 5/1998 | Andersen |
| 5,797,878 A | 8/1998 | Bleam |
| 5,800,392 A | 9/1998 | Racchini |
| 5,810,867 A | 9/1998 | Zarbatany et al. |
| 5,823,996 A | 10/1998 | Sparks |
| 5,866,561 A | 2/1999 | Ungs |
| 6,010,521 A | 1/2000 | Lee et al. |
| 6,030,405 A | 2/2000 | Zarbatany et al. |
| 6,048,332 A | 4/2000 | Duffy et al. |
| 6,126,634 A | 10/2000 | Bagaoisan et al. |
| 6,129,737 A | 10/2000 | Hamilton et al. |
| 6,149,641 A | 11/2000 | Ungs |
| 6,221,043 B1 | 4/2001 | Fischell et al. |
| 6,258,108 B1 | 7/2001 | Lary |
| 6,280,411 B1 | 8/2001 | Lennox |
| 6,344,028 B1 | 2/2002 | Barry |
| 6,383,212 B2 | 5/2002 | Durcan et al. |
| 6,413,203 B1 | 7/2002 | Sahatjian |
| 6,488,653 B1 | 12/2002 | Lombardo |
| 6,491,662 B1 | 12/2002 | Liprie et al. |
| 6,517,533 B1 | 2/2003 | Swaminathan |
| 6,540,734 B1 | 4/2003 | Chiu et al. |
| 6,544,221 B1 | 4/2003 | Kokish et al. |
| 6,544,223 B1 | 4/2003 | Kokish |
| 6,554,841 B1 | 4/2003 | Yang |
| 6,589,207 B1 | 7/2003 | El-Nounou |
| 6,623,452 B2 | 9/2003 | Chien et al. |
| 6,626,861 B1 | 9/2003 | Hart et al. |
| 6,659,977 B2 | 12/2003 | Kastenhofer |
| 6,696,121 B2 | 2/2004 | Jung, Jr. et al. |
| 6,733,474 B2 | 5/2004 | Kusleika |
| 6,733,486 B1 | 5/2004 | Lee et al. |
| 6,837,870 B2 | 1/2005 | Duchamp |
| 6,878,329 B2 | 4/2005 | Blankenship et al. |
| 6,881,216 B2 | 4/2005 | Di Caprio et al. |
| 6,896,842 B1 | 5/2005 | Hamilton et al. |
| 6,939,320 B2 | 9/2005 | Lennox |
| 6,942,680 B2 | 9/2005 | Grayzel et al. |
| 6,960,187 B2 | 11/2005 | Kastenhofer |
| 6,989,025 B2 | 1/2006 | Burgmeier et al. |
| 7,037,291 B2 | 5/2006 | Lee et al. |
| 7,048,714 B2 | 5/2006 | Richter |
| 7,115,299 B2 | 10/2006 | Kokish |
| 7,118,551 B1 | 10/2006 | Lee et al. |
| 7,179,251 B2 | 2/2007 | Palasis |
| 7,179,345 B2 | 2/2007 | Shkolnik |
| 7,195,611 B1 | 3/2007 | Simpson et al. |
| 7,225,518 B2 | 6/2007 | Eidenschink et al. |
| 7,351,238 B2 | 4/2008 | Lee et al. |
| 7,556,642 B2 | 7/2009 | Trotta |
| 7,625,353 B2 | 12/2009 | Grandt et al. |
| 7,628,769 B2 | 12/2009 | Grandt et al. |
| 7,658,723 B2 | 2/2010 | Von Oepen et al. |
| 2002/0042593 A1 | 4/2002 | Mickley et al. |
| 2002/0115982 A1 | 8/2002 | Barbut et al. |
| 2003/0032851 A1 | 2/2003 | Apple et al. |
| 2004/0122457 A1 | 6/2004 | Weber |
| 2004/0172121 A1 | 9/2004 | Eidenschink et al. |
| 2004/0181252 A1 | 9/2004 | Boyle et al. |
| 2004/0243158 A1 | 12/2004 | Konstantino et al. |
| 2004/0260239 A1 | 12/2004 | Kusleika |
| 2005/0288632 A1 | 12/2005 | Willard |
| 2006/0020256 A1 | 1/2006 | Bell et al. |
| 2006/0129178 A1 | 6/2006 | Reifart et al. |
| 2006/0149192 A1 | 7/2006 | Deniega et al. |
| 2006/0200110 A1 | 9/2006 | Lentz et al. |
| 2006/0224115 A1 | 10/2006 | Willard |
| 2006/0258987 A1 | 11/2006 | Lentz et al. |
| 2006/0287665 A1 | 12/2006 | Burton et al. |
| 2007/0060910 A1* | 3/2007 | Grandt et al. ................ 604/524 |
| 2007/0118076 A1 | 5/2007 | Lim et al. |
| 2007/0135830 A1 | 6/2007 | Schaeffer |
| 2008/0255507 A1 | 10/2008 | Mushtaha |
| 2008/0300610 A1 | 12/2008 | Chambers |
| 2009/0018502 A1 | 1/2009 | Reifart et al. |
| 2009/0254064 A1 | 10/2009 | Boatman |
| 2010/0069900 A1 | 3/2010 | Shirley et al. |
| 2011/0137245 A1 | 6/2011 | Schaeffer et al. |

FOREIGN PATENT DOCUMENTS

| | | |
|---|---|---|
| WO | WO 2006/074256 A1 | 7/2006 |
| WO | WO 2006/114783 A2 | 11/2006 |
| WO | WO 2006/136964 A1 | 12/2006 |
| WO | WO 2009/033026 A1 | 3/2009 |
| WO | WO 2009/036118 A1 | 3/2009 |
| WO | WO 2009/036135 A1 | 3/2009 |
| WO | 2010/120620 A1 | 10/2010 |

OTHER PUBLICATIONS

Koganemaru, Masamichi et al. "A Newly Developed Double Lumen Microballoon Catheter With a Side Hole: Initial Experience of Intraarterial Infusion Chemotherapy and/or Embolization." Published Online: Sep. 8, 2012, Japan Radiological Society.

* cited by examiner

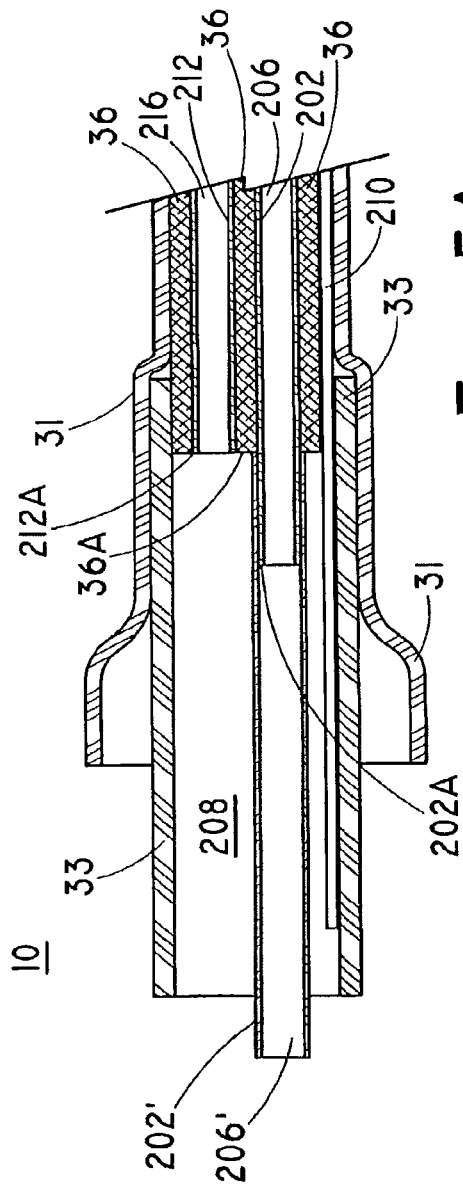
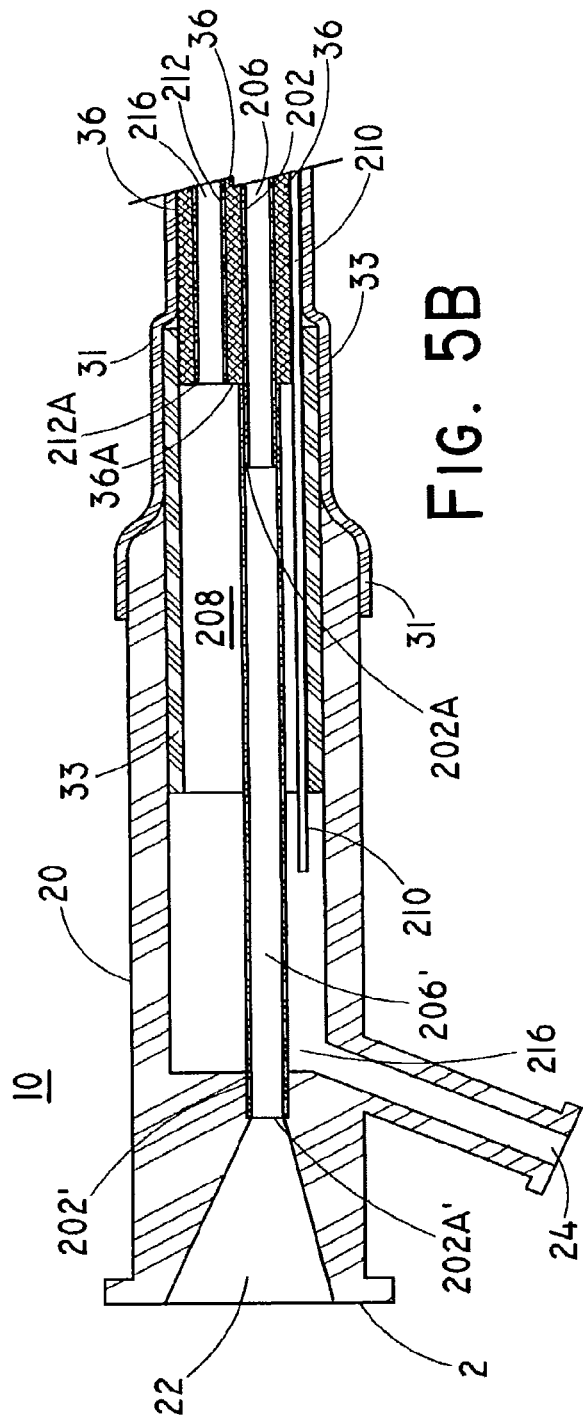
FIG. 5A
FIG. 5B

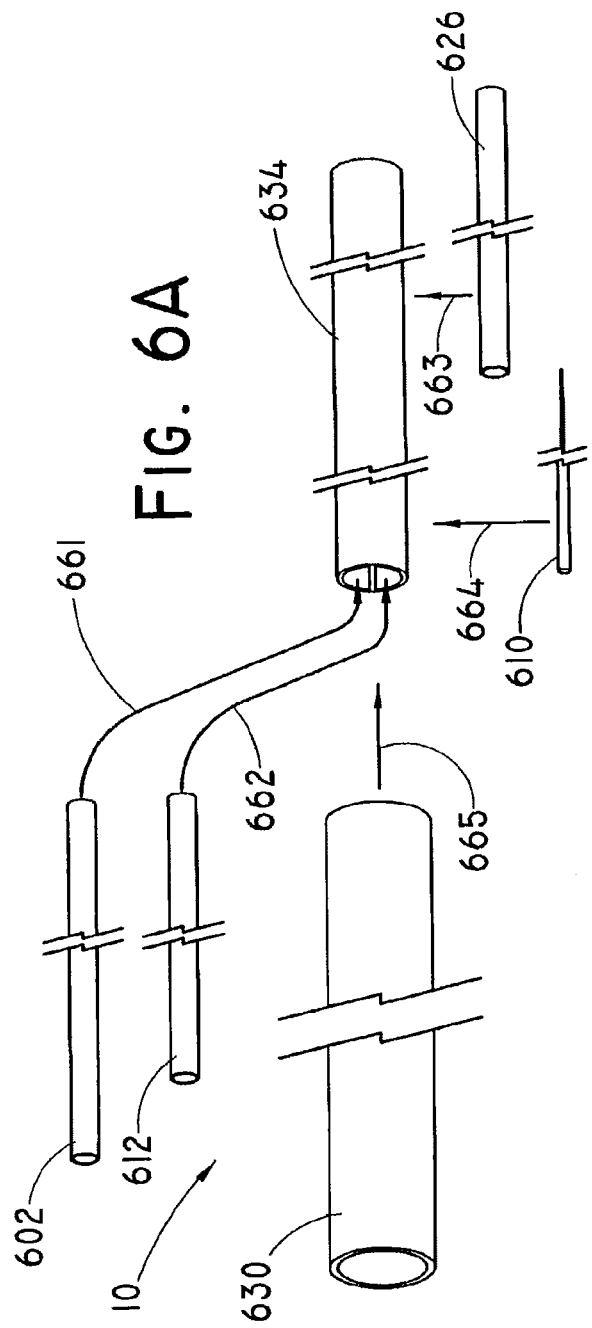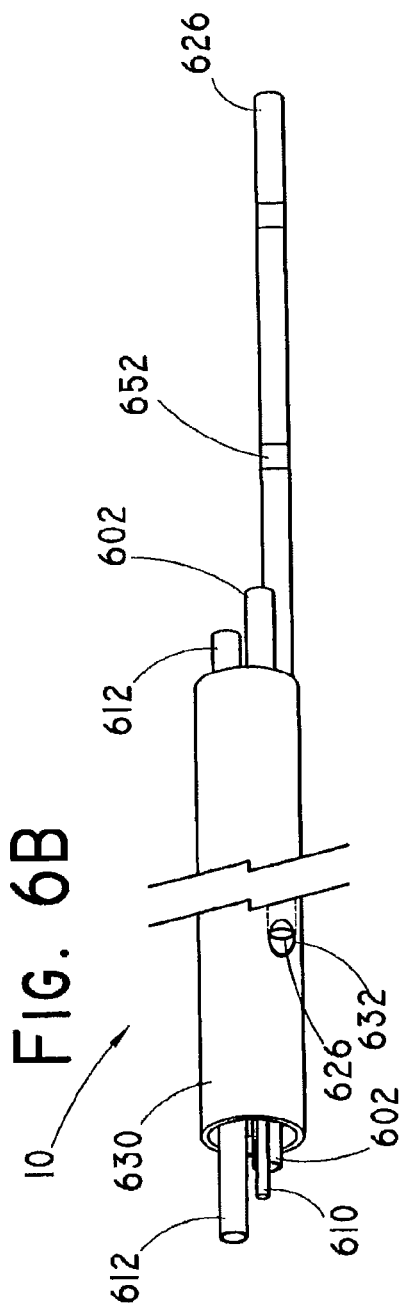

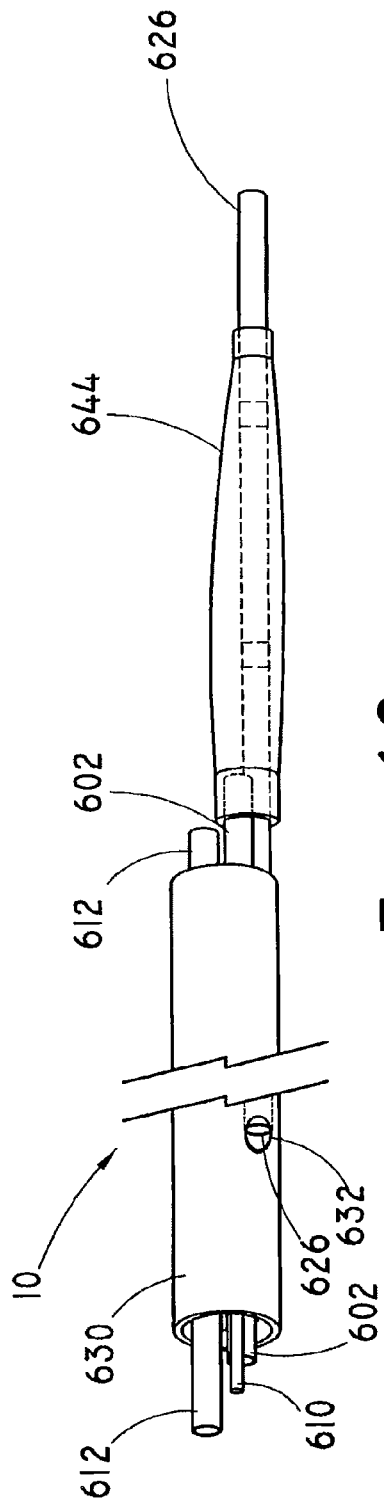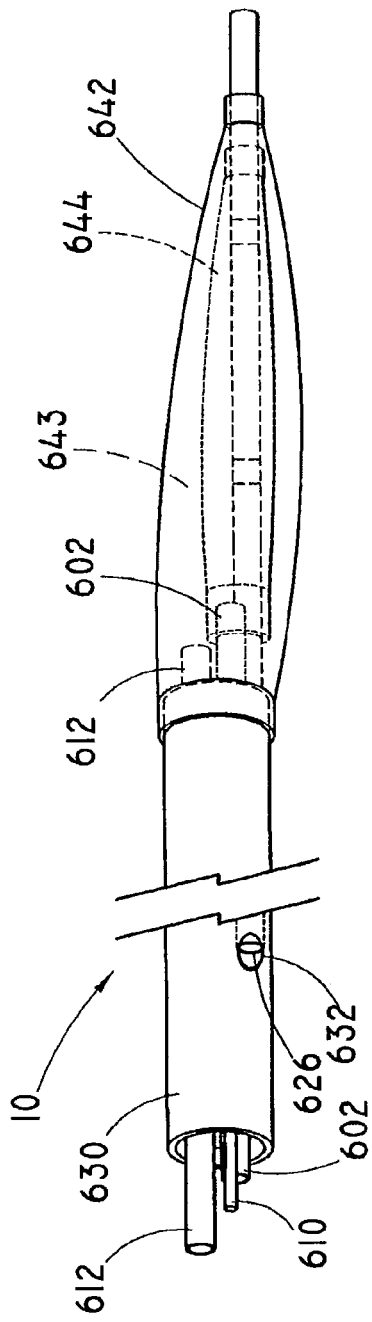

BALLOON CATHETER FOR DELIVERING A THERAPEUTIC AGENT

This application claims the benefit under 35 U.S.C. §120 as a continuation of U.S. patent application Ser. No. 12/676,786, filed Nov. 30, 2010, which claims the benefit under 35 U.S.C. §120 as a continuation of PCT Patent Application No. PCT/US08/75970, filed Sep. 11, 2008, which claims the benefit under 35 U.S.C. §119(e) of U.S. Provisional Application No. 60/971,802, filed Sep. 12, 2007, each of which are hereby incorporated by reference herein.

TECHNICAL FIELD

The present application relates to medical catheters and more specifically to medical catheters useful in delivering a therapeutic agent within a body vessel.

BACKGROUND

Although many medical conditions are satisfactorily treated by the general systemic administration of a therapeutic agent, the treatment of a many conditions require delivery of the therapeutic agent locally within a body vessel to a selected portion of internal body tissue, without delivery of the therapeutic agent to surrounding tissue or requiring systemic delivery of the therapeutic agent. A systemically administered therapeutic agent may be absorbed not only by the tissues at the target site, but by other areas of the body. As such, one drawback associated with the systemic administration of therapeutic agents is that areas of the body not needing treatment are also affected.

Medical delivery catheters provide a minimally invasive means for delivering therapeutic agents to internal body tissue. To provide site-specific localized treatment, balloon catheters may be used to deliver a therapeutic agent exclusively to the target site within a body vessel. One example of a condition that is beneficially treated by local administration of a therapeutic agent with a balloon catheter is the delivery of a therapeutic agent in combination with percutaneous transluminal coronary angioplasty (PTCA), a technique used to dilate stenotic portions of blood vessels. During PTCA, a catheter balloon is positioned at a blocked lumen or target site, the balloon is inflated causing dilation of the lumen. The balloon is deflated and the catheter is then removed from the target site and the patient's lumen thereby allowing blood to freely flow through the unrestricted lumen.

Although PTCA and related procedures aid in alleviating intraluminal constrictions, such constrictions or blockages may reoccur in many cases. The cause of these recurring obstructions, termed restenosis, may be due to the body responding to the surgical procedure. Restenosis of the artery commonly develops over several months after the procedure, which may require another angioplasty procedure or a surgical by-pass operation. Proliferation and migration of smooth muscle cells (SMC) from the media layer of the lumen to the intima cause an excessive production of extra cellular matrices (ECM), which is believed to be one of the leading contributors to the development of restenosis. The extensive thickening of tissues narrows the lumen of the blood vessel, constricting or blocking the blood flow through the vessel. Therapeutic agents selected to limit or prevent restenosis may be locally delivered with PTCA from a catheter and/or by placement of a stent configured to release the therapeutic agent after the PTCA procedure. Catheter balloons may be used in combination with stents, synthetic vascular grafts or drug therapies, during the PTCA procedure to reduce or eliminate the incidence of restenosis.

A number of catheter devices have been developed to administer a therapeutic agent locally to tissue while dilating a body vessel, such as during delivery of a therapeutic agent to a dilated portion of a coronary artery in a PTCA procedure. For instance, a therapeutic agent may be administered directly to the target site through small holes or apertures in the wall of a catheter balloon.

For example, U.S. Pat. No. 4,994,033 to Shockey et al. discloses a double balloon catheter for the application of medication to a blood vessel wall, for example to a stenosis. The distal portion of the catheter includes an inner balloon enclosed by a porous outer balloon. In operation, a therapeutic agent may be administered through a lumen in communication with the annular space between the inner and the outer balloon in the catheter, and is released through an array of minute holes or micropores in the outer balloon as the medication flows into the balloon through a lumen in the catheter shaft. The fluid medication is released by the action of pressurization in the lumen in communication with the outer balloon and forced out of the holes or micropores. However, at pressures of about 0.2 MPa (2 atmospheres) and above, the velocity of fluid that passes out of the holes of such a balloon often can create a forceful stream which directly impinges the arterial wall in a manner that may cause tissue damage.

U.S. Pat. No. 5,049,132 to Shaffer et al. describes a dual balloon catheter assembly having two concentric balloons in communication with separate lumens formed in the catheter shaft. A first non-perforated balloon is in communication with a first inflation lumen. A second, perforated, balloon is disposed around the first balloon and is in separate communication with a second inflation lumen. In addition, the catheter shaft may include a third separate lumen adapted to slidably house a guidewire for placement of the catheter assembly. However, the lumens of the catheter assembly are integrally formed in the catheter shaft, which may compromise tractability and pushability of the catheter system within a body vessel.

However, current fluid delivery catheters may suffer from a number of disadvantages that may limit the practical effectiveness of these devices, such as: (1) an inability to separately control the inflation of the balloon and the release of a liquid therapeutic agent, (2) increased diameter limiting the ability of the catheter to pass through a stenotic treatment site within a blood vessel (crossability), (3) undesirably compromised ability to curve while being translated within the blood vessel (tractability), (4) undesirably compromised ability to transmit a force when the balloon catheter is inserted into a blood vessel (pushability) or (5) an ability to inflate a dilation balloon on the distal portion of the catheter shaft to high pressures using a desirably flexible and low-profile catheter shaft. Kink resistance is an example of a characteristic relating to pushability. While reducing the profile (thickness) of catheter shaft may improve the crossability of the catheter, this may degrade pushability. Further, increasing rigidity of catheter shaft improves pushability and kink resistance, but tends to degrade crossability. In addition, the distal portion of the flow directed catheter must be extremely flexible so that it is capable of tracking the intricate vasculature to the site to be accessed under the influence of flow in the vessel. Consequently, conventional flow directed catheters have had distal portions formed of material which is extremely flexible, and which is also quite soft. Typically, the softer the material, the lower the burst pressure. Thus, some conventional fluid delivery catheters are formed with distal shaft portions with undesirably low burst pressure. This can cause the catheter to burst when injectant is introduced through the catheter. In other words, all the above-mentioned characteristics are closely related to each other, and it is not easy to improve all the characteristics at the same time while providing simultaneous independent control of the rate of drug delivery and inflation of a dual balloon catheter for delivering a therapeutic agent. There remains a need for a therapeutic balloon catheter for expanding a body vessel and administering medication to the body vessel wall while possessing improved or suitable catheter shaft burst pressure, crossability, pushability and tractability for an intended medical application.

SUMMARY

Balloon catheters adapted to delivery a therapeutic agent within a body vessel are described, as well as methods of manufacturing and using the balloon catheters. The balloon catheters may include a catheter shaft extending from a proximal end to a distal end. The catheter shaft preferably houses an inflation lumen spaced from a fluid delivery lumen in a side-by-side or coaxial orientation and may be formed in part by a thermoformable polymer. Preferably, the therapeutic agent is delivered across at least a portion of a balloon sealed to the distal portion of a catheter shaft. For example, a catheter balloon including a plurality of apertures may be mounted around at least a portion of the distal end of the catheter shaft. The balloon catheters may include one or more balloons and may also include a means for delivering a therapeutic agent through the catheter shaft through the plurality of apertures in the balloon and a means for expandably contacting the wall of a body vessel.

In a first embodiment, balloon catheter assemblies adapted for delivery of a therapeutic agent are provided herein. In particular, a balloon intraluminal drug delivery catheter assembly preferably includes a catheter shaft extending from a proximal end to a distal end including an outer sleeve disposed along a portion of the catheter shaft. The catheter shaft may include a first tubular member defining an inflation lumen and a second tubular member defining a fluid delivery lumen. The first and second tubular members can be each disposed within the outer sleeve and can extend through at least a portion of the catheter shaft, with the first and second tubular members being adjacent with respect to each other. The catheter shaft may be formed in part by a thermoformable polymer. A first balloon may be mounted on the distal end of the catheter shaft in communication with the inflation lumen. A second balloon may be mounted around at least a portion of the first balloon on the distal end of the catheter shaft in communication with the fluid delivery lumen. An annular balloon fluid delivery lumen may be defined between the first balloon and the second balloon. Preferably, the first balloon and the second balloon are not attached within the annular balloon fluid delivery lumen disposed therebetween. The second balloon may include an aperture means for releasing fluid from the fluid delivery lumen. The aperture means can include a plurality of apertures being disposed along a longitudinal portion of the second balloon and having a total cross sectional area that increases in a distal longitudinal direction along the second balloon. The second balloon may be an outer balloon and the first balloon may be an inner balloon. The balloons may be formed from the same or different materials, but are preferably formed from one or more semi-compliant polyamide material(s) having substantially equal Young's modulus.

In a first aspect of the first embodiment, the balloon catheter assembly further includes a stiffening member within a portion of the catheter shaft. The stiffening member can be disposed within the outer sleeve adjacent with respect to the first and second tubular members, with a portion of the stiffening member being surrounded by the thermoformable polymer, where the stiffening member is in non-translatable contact with the thermoformable polymer. At least a distal portion of the stiffening member may include a tapered member with a transverse cross-sectional area that decreases along the distal longitudinal direction. The stiffening member is preferably configured to provide improved pushability to the catheter assembly. The stiffening member may be integrally formed within the thermoformable polymer, rather than being introduced to a lumen within a catheter shaft, and is preferably included in the proximal portion of a "short-wire" ("rapid exchange") catheter configuration. Typically, the stiffening member extends from the proximal manifold of a catheter assembly past a wire guide aperture located along the catheter shaft. The stiffening member may be formed from a suitably rigid material, such as stainless steel.

In a second aspect of the first embodiment, the second balloon aperture means includes the plurality of apertures with a total cross sectional area that increases in a distal longitudinal direction along the outer balloon so as to reduce the injection pressure required to deliver the therapeutic agent. The total cross sectional area of the plurality of apertures may be increased in the distal longitudinal direction by increasing at least one of the size of the apertures and the density of the apertures along the distal longitudinal direction along the second balloon. Typically, inflation of the first balloon reduces the volume of an annular balloon fluid delivery lumen between the first balloon and the second balloon, providing additional resistance to the injection of a fluid containing the therapeutic agent into the catheter shaft and through the apertures in the outer balloon. By providing a plurality of apertures in the second balloon having increasing cross sectional area in the distal direction, fluid may be delivered more uniformly along the length of the second balloon.

To improve the physical attributes of the catheter assembly, such as pushability, tractability, and/or resistance to rupture during inflation and/or drug delivery, each of the lumens in the catheter shaft are preferably lined with a fluorinated hydrocarbon, such as PTFE. The lumens are preferably oriented in a side-by-side configuration along the catheter shaft. The drug delivery balloon catheter may include (1) a first fluorinated hydrocarbon tubular liner positioned within the catheter shaft and defining the inflation lumen, (2) a second fluorinated hydrocarbon tubular liner positioned within the catheter shaft and defining the fluid delivery lumen, and (3) a wire guide lumen formed by a third fluorinated hydrocarbon tubular liner. The third tubular liner preferably has a thickness greater than that of the first tubular liner or the second tubular liner. The catheter shaft may include a first portion having the inflation lumen and the fluid delivery lumen in a coaxial configuration and a second portion having the inflation lumen and the fluid delivery lumen in a side-by-side configuration. The thermoformable polymer in the catheter shaft preferably has a lower melting temperature than the fluorinated hydrocarbon tubular liner. The outer sleeve may comprise a cross-linked heat-shrinkable polymer, such as PEBA, around the thermoformable polymer, the tubular liners and the stiffening member. The burst pressure of the catheter shaft comprising one or more fluorinated hydrocarbon tubular liner(s) may be greater than the burst pressure of the tubular liners themselves. In one aspect, the burst pressure of a catheter assembly comprising each of the outer sleeve and the first and second tubular members, that may comprise a fluorinated hydrocarbon tubular liner, and thermoformable polymer disposed therebetween has a greater burst pressure than the burst pressures of any one of the tubular members, thermoformable polymer or outer sleeve. Preferably, the burst pressure of the catheter assembly shaft is at least about 2.7-3.5 MPa (27-35 atmospheres).

In a second embodiment, methods of manufacturing a balloon drug delivery catheter with improved tractability and pushability are provided. The methods may include the step of aligning a first tubular member, a second tubular member, and/or a third tubular member substantially parallel and laterally spaced apart with respect to each other, where each tubular member defines a lumen extending from a proximal end to a distal end and formed from a fluorinated hydrocarbon. The tubular members and/or a stiffening member may be disposed within an outer sleeve and joined in a fixed orientation to one another within a thermoformable polymer contacting each tubular member and/or the stiffening member to form the catheter shaft by applying heat to melt the thermoformable polymer and to shrink the outer sleeve formed from a cross-linked heat-shrinkable polymer. Preferably, the stiffening member is fixed in non-moveable contact with the thermoformable polymer forming the catheter shaft between the lumens therein. A first expandable material may be attached to the distal end of the catheter shaft to form an inner balloon in fluid communication with the distal end of the first tubular member, and a second expandable material may be attached to the distal end of the catheter shaft around the inner balloon to form an annular lumen between the outer balloon and the inner balloon, an annular lumen formed therebetween being in fluid communication with the distal end of the second tubular member. A plurality of apertures may be formed in the second expandable material before, during or after forming the outer balloon. The plurality of apertures may have a total cross sectional area that increases in a distal direction along the outer balloon.

BRIEF DESCRIPTION OF THE DRAWINGS

FIG. 5A is a longitudinal cross sectional view of the proximal catheter shaft portion of a balloon catheter assembly.

FIG. 5B is a longitudinal cross sectional view of a manifold attached to the proximal catheter shaft portion of a balloon catheter assembly.

FIG. 6A is a first exploded view of a portion of a balloon catheter assembly.

FIG. 6B is a second exploded view of a portion of a balloon catheter assembly.

FIG. 6C is a third exploded view of a portion of a balloon catheter assembly.

FIG. 6D is a fourth exploded view of a portion of a balloon catheter assembly.

DETAILED DESCRIPTION

Figure 1:
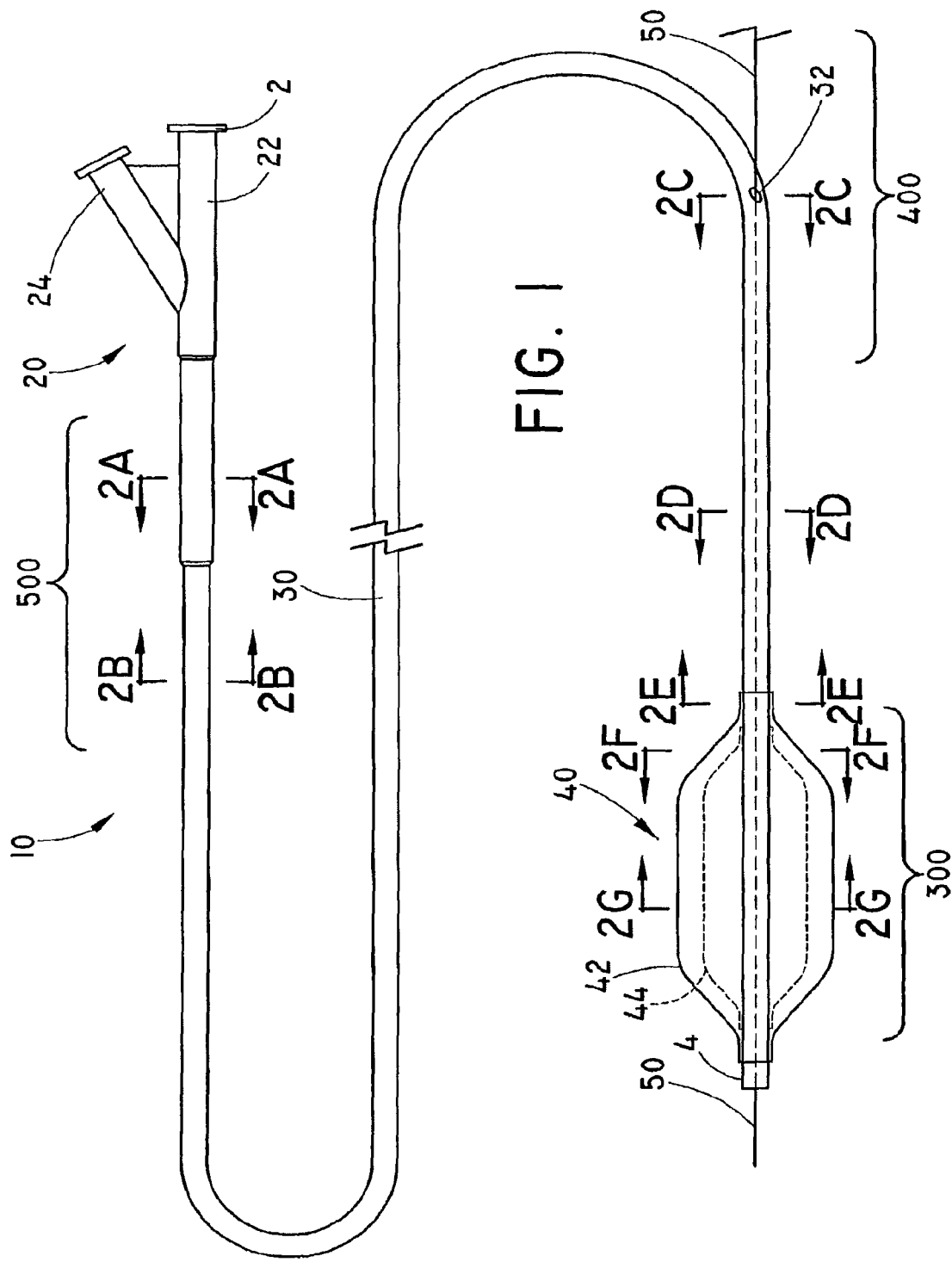
FIG. 1 is a perspective view of a balloon catheter assembly with multiple balloons.

The present disclosure relates to a balloon catheter assembly for delivering a therapeutic agent to a body vessel, as well as methods of manufacturing the same and methods of treatment using the balloon catheter assembly. For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As used herein, the terms "proximal" and "distal" describe longitudinal directions in opposing axial ends of the balloon catheter assembly, and components thereof. The term "proximal" is used in its conventional sense to refer to the end of the device (or component) that is closest to the operator during use. The term "distal" is used in its conventional sense to refer to the end of the device (or component) that is initially inserted into the patient, or that is closest to the patient.

As used herein, the term "therapeutic agent" refers to any medically beneficial compound that may be delivered by a balloon catheter assembly in a fluid form. Preferably, the therapeutic agent is an agent effective to treat or prevent restenosis, such as an antisense agent, a microtubule stabilizing agent or an inhibitor of the mammalian target of rapamycin (mTOR). Preferred antisense compounds include the NeuGene Antisense compounds sold as Resten-NG and Resten-MP by AVI Biopharma, as well as rapamycin, paclitaxel and various analogs or derivatives thereof. Other preferred therapeutic agents are described in U.S. Pat. No. 7,094,765, incorporated herein by reference. Most preferably, the therapeutic agents include an antisense molecule having a morpholino antisense compound with uncharged phosphorus-containing backbone linkages, and spanning the start codon of a human c-myc mRNA.

As used herein and unless otherwise indicated, the term "thermoformable" refers in general to a material that may be reshaped under conditions of temperature and/or pressure. Preferably, a thermoformable polymer may be softened or melted under processing conditions to adhere to adjacent structural components. For example, a catheter shaft assembly may include a thermoformable polymer contacting one or more tubular liners and/or a stiffening member. Upon heat and/or pressurized processing of the catheter shaft assembly, the thermoformable polymer may melt or soften, adhering the tubular liners and/or stiffening member to one another. Preferably, the thermoformable polymer has a flowability above a desired processing temperature, but forms a solid having desired resilience and strength properties at a temperature of intended use (e.g., 37° C. (98.6° F.). The catheter shaft may include a thermoformable polymer that adheres to and fills the voids between structural components therein, such as fluorinated hydrocarbon tubular members and/or a stainless steel stiffening member.

In a first embodiment, a balloon catheter assembly for delivering a therapeutic agent is provided as shown in FIG. 1. The balloon catheter assembly 10 extends from a proximal end 2 to a distal end 4. Therebetween, the balloon catheter assembly 10 includes manifold 20 (further described with respect to FIGS. 5A-5C), a proximal region 500 (further described with respect to FIGS. 2A, 2B and 5) of the catheter shaft 30, an intermediate region 400 (further described with respect to FIGS. 2C and 3B) of the catheter shaft 30 and a distal region 300 (further described with respect to FIGS. 2E, 2F, 2G, 3A and 4) of the catheter shaft 30 that includes a dual balloon assembly 40.

The manifold 20 is operatively joined to a catheter shaft 30 in a proximal region 500. The manifold 20 may include a lateral injection port 24 and an inflation port 22. The catheter shaft 30 may also include one or more conventional fittings and/or adapters between the manifold 20 and the proximal end of the catheter shaft 30. The balloon catheter assembly 10 is a "short wire" system having a wire guide port 32 within an intermediate region 400 of the catheter shaft 30, providing access to a wire guide lumen extending through the catheter shaft 30 from the wire guide port 32 to the distal end 4 of the catheter shaft 30. Alternatively, the balloon catheter assembly 10 may be an "over the wire" system with the wire guide port 32 positioned proximate the proximal end 2 of the catheter shaft 30 or as part of the manifold 20. That is, the manifold 20 may include the wire guide port 32 in addition to the inflation port 22 and the injection port 24. The distal region 300 of the balloon catheter assembly 10 includes a perforated outer balloon 42 radially disposed around an inner inflation balloon 44. The inner balloon 44 is preferably non-porous and in fluid communication with the inflation port 22 through the body of the catheter shaft 30. The outer balloon 42 is in fluid communication with the injection port 24 through the catheter shaft 30 and separated from both the inner balloon 44 and the inflation port 22. An annular lumen for receiving a therapeutic agent from the injection port 24 may be formed between the inner balloon 44 and the outer balloon 42. Both the inner balloon 44 and the outer balloon 42 may be sealed to the distal end 4 of the catheter shaft 30, within the distal portion 300 of the catheter shaft 30 housing the distal portion of the wire guide lumen. The balloon catheter assembly 10 may be translated over a wire guide 50 shown extending from the wire guide port 32, through the catheter shaft 30 and extending from the distal end 4 of the catheter shaft 30. The balloon catheter assembly 10 is typically provided separately from the wire guide 50, an introducer sheath (not shown) or other devices typically used to insert the balloon catheter assembly 10 within a body vessel.

In operation, the balloon catheter assembly 10 may be introduced to a body vessel by conventional medical procedures, such as the Seldinger technique, and subsequently translated through the body vessel over the wire guide 50 to position the distal region 300 at a point of treatment therein. The inner balloon 44 may be inflated to a desired diameter by injecting a suitable inflation fluid, such as a pressurized air, gas or liquid, through the inflation port 22 in the manifold 20. For example, the inner balloon 44 may be inflated to expand a stenosis in a body vessel such as a coronary artery. Preferably, the inner balloon 44 is inflated until the outer balloon 42 contacts a portion of a body vessel wall at a point of treatment.

A fluid containing a therapeutic agent and/or a diagnostic agent (e.g., x-ray contrast media) may be injected through the injection port 24, transported within the catheter shaft 30 and introduced to the annular lumen between the outer balloon 42 and the inner balloon 44. The therapeutic agent fluid may be pressurized to deliver the therapeutic agent to the wall of a body vessel through openings in the outer balloon 42 before, during or after inflation of the inner balloon 44.

In a first aspect of the first embodiment, the catheter shaft 30 is formed from a thermoformable material enclosing one or more tubular members. The tubular members may be formed from a material having a higher melting temperature than the thermoformable material, and may be secured within the catheter shaft by melting or softening the thermoformable material around the outside of the tubular members, without blocking the lumen extending through each tubular member. Preferably, the tubular members are formed from a fluorinated hydrocarbon, such as PTFE or FEP, or a polyimide. The thermoformable material is preferably a polymer, and may include a PEBA polymer or other lower-melting point polymer with a desired level of rigidity and flexibility for forming the catheter shaft 30. The catheter shaft 30 may include tubular members (e.g., 202, 212) having a substantially uniform inner diameter. The wall of the tubular members preferably has a thickness adequate to prevent bursting of the tubular member during inflation and/or delivery of a therapeutic agent fluid. The tubular members are most preferably formed from a fluorinated hydrocarbon, such as poly(tetrafluoroethylene) (PTFE).

Figure 2A:
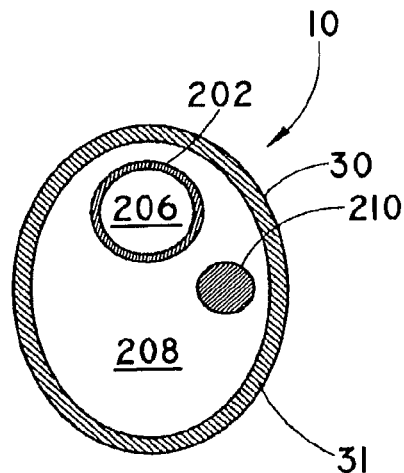
FIG. 2A is a transverse cross-sectional view of along line 2A-2A of the balloon catheter assembly shown in FIG. 1.

In a second aspect of the first embodiment, a proximal portion of the catheter shaft 30 may include a stiffening member (210) to improve the pushability of the balloon catheter assembly 10. FIG. 2A is a first cross-sectional view of the catheter shaft 10 along line A-A'. The outer surface of the catheter shaft 30 encloses a first tubular member 202 and a stiffening member 210 positioned within a proximal inflation lumen 208 defined by the inner wall of the catheter shaft 30, proximate the transition from the proximal catheter shaft portion. The first tubular member 202 defines an inflation lumen 206 extending from a proximal end 202a in communication with the inflation port 22 in the manifold 20 to a distal end 202b in communication with the inner balloon 44 at the distal portion 300 of the balloon catheter assembly 10. The stiffening member 210 (as shown in transverse cross section A-A' in FIG. 2A) may be included within a catheter shaft 30 having a wire guide port 32 positioned between the manifold 20 and the distal end 4 of the balloon catheter assembly 10. The stiffening member 210 is preferably sealed within a proximal portion of the catheter shaft 30, rather than being inserted into a lumen of the catheter shaft 30. To enhance the pushability of the balloon catheter assembly 10, the stiffening member 210 is preferably not moveable with respect to the balloon catheter assembly 10. For example, the stiffening member 210 may be integrally formed with the catheter shaft 30 by a thermoformable material 36 that is melted or softened to surround and secure the catheter shaft 30 within the proximal region 500 of the catheter shaft 30 (see, e.g., FIG. 2B). The stiffening member 210 can be formed from any material, and has any suitable dimension, providing a desired level of rigidity to impart a desired level of pushability to the catheter shaft 30 without undesirably reducing the tractability. The stiffening member 210 may be a tapered mandrel having a cross sectional area that decreases in the distal direction along the catheter shaft 30. For example, a stiffening member may be formed from a 0.038 mm (0.015-inch) diameter proximal end tapered to a distal end with a diameter of about 0.05 mm (0.002-inch). Examples of suitable stiffening member materials include stainless steel, nickel-titanium alloy, cobalt-chromium alloy, and stiff polymers such as poly(tetrafluoroethylene) (PTFE), high density polyethylene (HDPE) and polyether ether ketone (PEEK), and other rigid materials. U.S. patent application Ser. No. 11/429,845 describes another example of a stiffening member construction suitable for use within the catheter shaft 30.

Referring to FIG. 2A, the catheter shaft 30 may be formed from any suitable material, but preferably includes a thermoformable material 36. The catheter shaft 30 may comprise an outer sleeve 31 formed as an extruded sleeve, shrink tube, extruded over-jacket, or dip coat. The catheter shaft 30 is preferably a thermoformable material 36 and may comprise polymers, for example, HDPE, PTFE, PET, polyester or polyether block amide (PEBA), polyurethane, polyimide, polyolefin, nylon, or any combination thereof. The catheter shaft is preferably formed of a PEBA polymer outer sleeve 31 enclosing the tubular members 202, 212, 222. The outer sleeve 31 may be applied by, for example, over-extrusion, dip-coating, melt fusion, or heat shrinking. For example, the outer sleeve 31 may be a PET shrink tube. The type of material may also be selected to complement other catheter components; for example, a nylon sleeve may bond and interact better with a nylon expandable member such as a balloon or basket and/or a nylon wire guide lumen. Selection of coating materials and diameter allow manipulation of the shore hardness of the catheter shaft 30, which offer the desired functional properties.

The balloon catheter assembly 10 may be configured with a desirably small outer diameter, a sufficiently flexibility to pass through a tight curvature or tortuous passageway, and a pushability and tractability sufficient to be navigated through such tightly curved and/or tortuous pathways in the same manner as a wire guide. A preferred outer diameter will be different for different applications, but the outer diameter a catheter embodiment configured for use in peripheral blood vessels may be in the range of about 1.0-1.4 mm (0.040-0.055 inches), and that the outer diameter may differ along the length of the catheter embodiment. The catheter shaft 30 may optionally be configured as a rapid exchange catheter, as shown in FIG. 1. The outside diameter of the catheter shaft 30 is typically approximately 1-1.5 mm (0.04-0.059 inches). A preferred catheter shaft 30 tapers from a greater proximal outer diameter (such as, for example, about 1.2 mm (0.048 inches) to about 1.3 mm (0.052 inches) to a lesser (reduced) distal diameter (such as, for example, about 1.1 mm (0.044 inches) to about 1.0 mm (0.040 inches). The lesser distal diameter may present improved tractability for navigation of tortuous passages.

The catheter shaft 30 may optionally further include a coating on the outer sleeve 31. A preferred coating may provide a desirable lubricity profile that exhibits low friction during introduction of the device through, for example, a blood vessel. A preferred coating may also provide a fluid-tight seal configured to prevent leakage of pressurized inflation fluid (for example, at pressures in a normal operating range up to about 0.8-1.4 MPa (8-14 atm), and preferably configured to prevent leakage at pressures exceeding normal ranges, for example, up to or exceeding about 2.7 MPa (27 atm)). The coating may be a thermoplastic polymer such as, for example, a polyester or polyether block amide (e.g., PEBAX®).

Figure 2B:
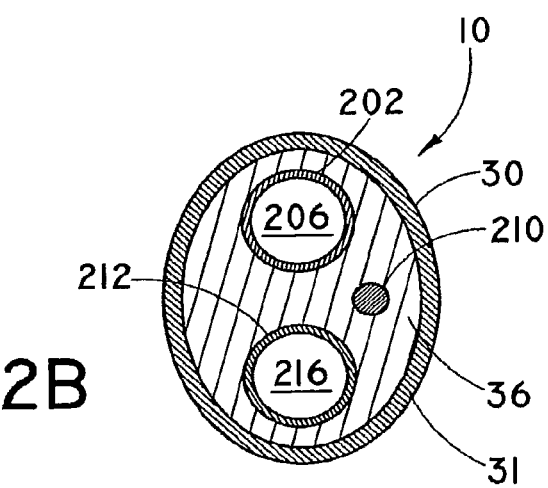
FIG. 2B is a transverse cross-sectional view of along line 2B-2' of the balloon catheter assembly shown in FIG. 1.

FIG. 2B is a second transverse cross-sectional view of the catheter shaft 10 along line B-B' in FIG. 1, positioned longitudinally distal to line A-A'. A second tubular member 212 defining a fluid delivery lumen 216 is positioned within the catheter shaft 30, beside the first tubular member 202 and stiffening member 210 described above. The fluid delivery lumen 216 extends from a proximal end 212a attached to the manifold 20 to a distal end 212b in communication with an annular balloon fluid delivery lumen 242 inside the outer balloon 42. A thermoformable material 36 fills the body of the catheter shaft between the tubular members (202, 212), the stiffening member 210 and an outer sleeve 31. Preferably, the second tubular member 212 is similar to the first tubular member 202, except that the proximal end of the second tubular member 212 is positioned distal to the proximal end of the first tubular member 202. The stiffening member 210 in FIG. 2B may have a smaller cross-sectional area than in FIG. 2A, due to tapering of a distal portion of the stiffening member 210 in the distal longitudinal direction. Alternatively, the tapering of the stiffening member 210 may begin distal to the cross-section of FIG. 2B and proximal to FIG. 2C. Preferably, the inflation lumen 206 and the fluid delivery lumen 216 remain oriented side-by-side and substantially parallel to one another for at least a portion of the catheter shaft 30. The first tubular member 202 and the second tubular member 212 may be formed from the same or similar material and may have similar or identical inner diameters (e.g., about 0.36 mm (0.014-inch)) and thicknesses (e.g., about 0.064 mm (0.0025-inch)).

Figure 8:
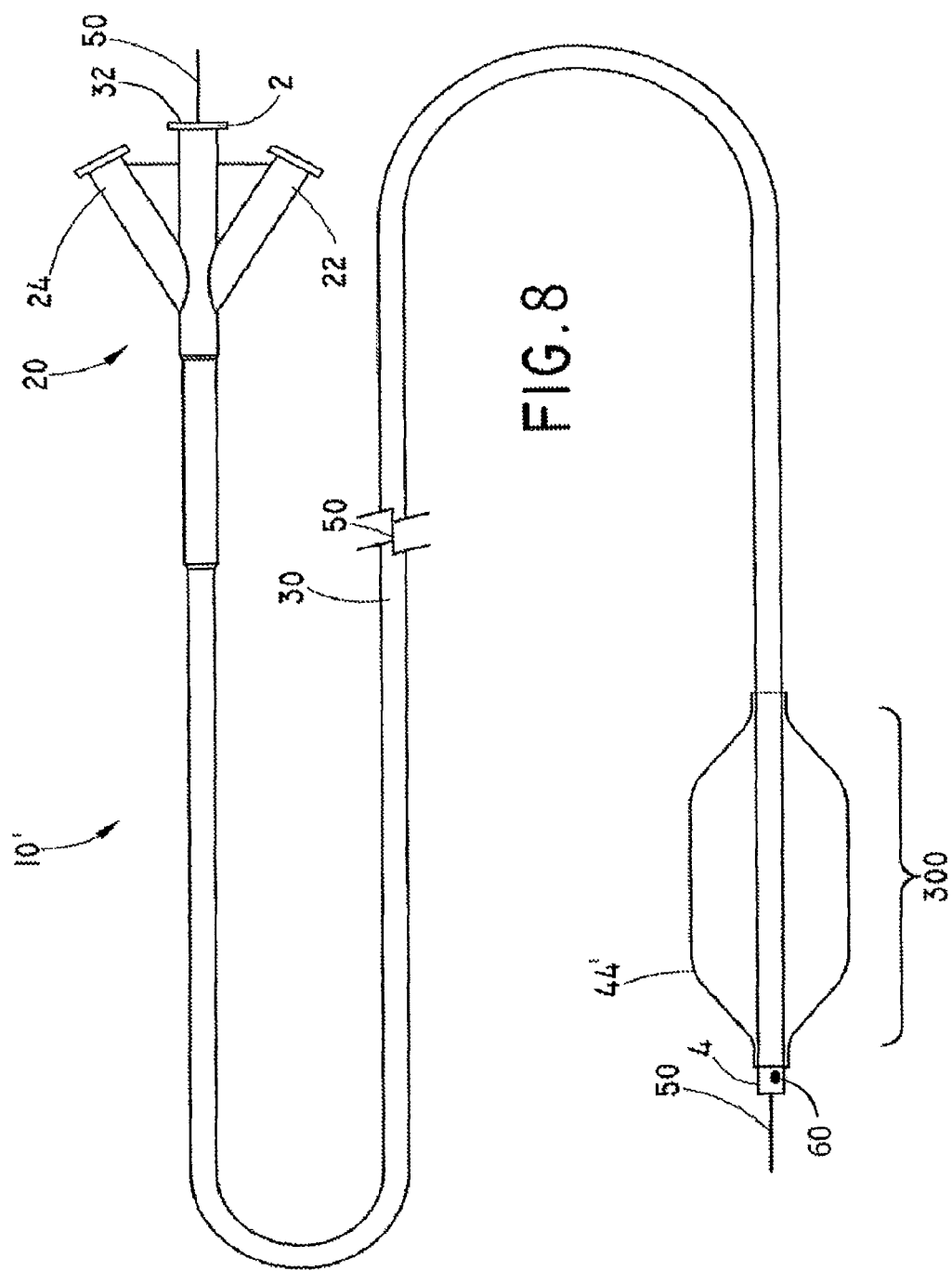
FIG. 8 is a perspective view of a balloon catheter assembly having a single balloon.

In one example, to form the catheter shaft 30, the first tubular member 202 and the second tubular member 212 may be placed within each of the two lumens of a dual lumen thermoplastic sleeve formed from a thermoformable material 36 and having a "figure 8" transverse cross section defining two lumens with a wall thickness of at least about 0.064 mm (0.0025-inches) between the two lumens. Optionally, each of the tubular members 202, 212 may be supported within the thermoplastic sleeve lumens on separate temporary mandrels while being inserted into the thermoplastic sleeve. The thermoplastic sleeve lumens may have any suitable inner diameters to receive the tubular members 202, 212, such as between about 0.038 mm (0.0015-inches) and 0.051 mm (0.0020-inches). Optionally, the thermoplastic sleeve may include a first lumen and a second lumen with substantially identical inner diameters. Alternatively, the thermoplastic sleeve may include a first lumen with an inner diameter of about 0.038 mm (0.0015-inches) and a second lumen with an inner diameter of about 0.046-0.064 mm (0.0018-0.0025-inches). Both lumens within the thermoplastic sleeve are preferably substantially parallel to one another and extend along the entire length of the thermoplastic sleeve. The dual-lumen thermoplastic sleeve may be constructed of a thermoformable material 36 such as, for example, a polyolefin, polyester or polyether block amide (PEBA), or other appropriate polymeric material that may be heated to flow around and join together the tubular members 202, 212 within the lumens of the thermoplastic sleeve to the stiffening member 210 and a third tubular member 222 positioned adjacent the thermoplastic sleeve (i.e., external to the lumens of the thermoplastic sleeve but within the outer sleeve 31).

As indicated above, to further improve pushability and tractability of the balloon catheter assembly 10, the stiffening member 210 is preferably integrally joined to the tubular members 202, 212 along side the thermoplastic sleeve, with the tapered distal end of the stiffening member distal (e.g., 5 cm mm) to the wire guide port 32. Preferably, the stiffening member 210 is not inserted through a lumen within the thermoplastic sleeve, but rather, is integrally formed within the catheter shaft after heat processing of the thermoplastic sleeve to permit a thermoformable material 36 flow around the stiffening member 210 and the tubular members 202, 212, 222 during processing to form a single catheter shaft after heat and/or pressure processing. The stiffening member 210 may be positioned outside the thermoplastic "figure 8" sleeve but inside the outer sleeve 31. The outer sleeve 31 may be formed of any suitable heat-shrinkable material that is capable of forming a secure bond with the dual-lumen thermoplastic sleeve and/or one or more of the tubular members 202, 212, 222.

The catheter shaft 30 may be formed by enclosing the dual-lumen thermoplastic sleeve having the "figure-8" cross-section defining a first lumen and a second lumen and the stiffening member 210 within the outer heat-shrinkable sleeve. A heat shrinkable outer sleeve 31 may be placed around the thermoplastic sleeve, the tubular members 202, 212, 222 and the stiffening member 210. The outer sleeve 31 typically has a higher melting point than that of the thermoformable material 36 of the thermoplastic sleeve. When the thermoplastic sleeve comprises a nylon or PEBA, a preferred outer sleeve 31 material comprises a copolymer, and more preferably, a block copolymer such as a cross-linked polyether block amide (PEBA). Block copolymers comprise alternating segments formed of a harder, or more crystalline material, and a softer, or more amorphous, material. When the copolymer is PEBA, the harder material comprises a polyamide, such as nylon 12, and the amorphous segments comprise polyether. The hard and the amorphous segments are linked together by urethane groups in known fashion. By varying the ratio of the polyamide to polyether blocks, PEBA compositions of varying properties, such as melting point, dimensional stability, hardness, etc., may be created. Commercially available grades of PEBA typically have a Shore hardness between about 72D and 75A. Higher polyamide to polyether ratios will result in a higher Shore hardness (stiffer material), and lower polyamide to polyether ratios result in a lower Shore hardness (softer material).

Typically, the outer sleeve 31 comprises a thermoplastic material that is subjected to at least partial cross-linking. The thermoformable material 36 is preferably free of crosslinking or has a reduced degree of cross linking compared to the outer sleeve 31. When a polymeric material is cross-linked, chemical links are established between the molecular chains of the polymer, thereby resulting in a change of properties in the cross-linked material when compared to the non-cross-linked material. In general, when a material is cross-linked, the properties of the cross-linked material cause it to behave more in the nature of a thermoset material. Thus, the resulting material may have higher dimensional stability (hoop strength), higher tensile strength, higher stiffness and density, higher melting temperature, improved heat memory, improved chemical resistance, and improved physical strength, among other properties, when compared to the non-cross-linked thermoplastic. Similarly, some properties, such as elongation and the ability to flex, are generally lower in the cross-linked material when compared to the non-cross-linked material. Thus, for example, when the cross-linked material is a block copolymer such as PEBA, the properties of the resulting cross-linked material will generally differ from those of the original block copolymer in the manner described above. It is often desirable to control the amount, or degree, of cross-linking of a particular block copolymer in order to optimize the desired properties of the cross-linked polymer. In some instances a trade-off must be made to arrive at a copolymer that is sufficiently cross-linked to be effective for its intended purpose, but not so highly cross-linked as to effectively negate the beneficial results of the cross-linking.

The outer sleeve 31 preferably includes a cross-linked PEBA polymer, while the thermoformable material 36 is preferably a non-cross-linked PEBA polymer. Cross-linking procedures are well known in the arts. Typically, cross-linking is initiated by chemical means, or by irradiation. With chemical initiation, an initiating compound, such as a peroxide, is mixed into the matrix of the polymer. With irradiation, a material is exposed to high-energy radiation to initiate the formation of the molecular bonding. Both of these methods have been found to effectively promote molecular bonding within the material. In modern practice, irradiation is probably the more common mode for initiating the cross-linking reaction. Examples of procedures involving the cross-linking of polymeric compositions for use in medical applications are discussed, e.g., in U.S. Pat. No. 6,663,646 and U.S. Pat. No. 6,596,818, the disclosures of which are incorporated by reference herein. The outer may include other cross-linkable polymers, with or without PEBA. A copolymer may be formed of alternating hard blocks and amorphous blocks. Similarly, the copolymer may be selected such that following cross-linking, the copolymer has a sufficient number of non-cross-linked active sites (analogous to the amide sites on the PEBA copolymer) that are capable of forming a secure bond with the adjoining inner layer of the sheath. A non-limiting list of other polymeric compositions that may be utilized as an outer heat shrink layer under appropriate conditions includes polyolefins, PET and FEP.

The assembly of the tubular members, the dual-lumen thermoplastic sleeve and the outer heat-shrinkable sleeve can be joined together by heating a catheter assembly to a temperature suitable to melt or soften the thermoformable material 36 and shrink the outer sleeve 31, but below a temperature effective to melt or soften the tubular members 202, 212. Upon exposure to a controlled amount of heat, the thermoformable material 36 may melt and flow between the interstices within the outer sleeve 31, and is fused to the outer surfaces of the tubular members 202, 212, 222 and the stiffening member 210. The outer sleeve 31 may compress the thermoformable material 36, the tubular members 202, 212, 222 and the stiffening member 210 together to form the catheter shaft 30 in a conventional manner when heat shrink techniques are used to form the catheter shaft 30. Those skilled in the art will appreciate that the outer sleeve 31 and a polymeric thermoformable material 36 may be formed from a variety of medical grade materials suitable for such purposes, so long as the layers are capable of being fused or otherwise bonded or securely attached to each other upon the application of heat, as described. The temperature may vary widely, depending on material. Polyolefin has a low shrink temperature of about 290° F. (143° C.), however it can withstand temperatures up to about 450° F. (232° C.). PET shrinks at 302° F. (150° C.) but melts at 374° F. (190° C.). PEBA shrinks at 340° F. (171° C.) and will not degrade at temperatures under about 500° F. (260° C.). FEP shrinks at 375° F. (190° C.), but does not degrade until temperatures exceed 600° F. (315° C.). For example, the catheter assembly may be heated to a temperature of about 400-550° F. (204-288° C.) and preferably about 500° F. (260° C.), to join the dual-lumen sleeve comprising the thermoformable material 36, the two tubular members 202, 212 and the stiffening member 210 within the heat-shrinkable outer sleeve 31 to form the balloon catheter assembly 10. If present, the temporary mandrels may be removed from the lumens of the tubular members 202, 212 after heat processing to join the assembly together. Optionally, the assembly may be heated while enclosed in a suitable bonding sleeve, such as an FEP heat shrink material, to provide heat-transmitting contact to the outer sleeve 31 during processing. The bonding sleeve may later be removed along with any temporary mandrels within the tubular members 202, 212.

The balloon catheter assembly 10 is preferably configured as a "short-wire" configuration, where the wire guide lumen 226 may not extend the entire length of the catheter shaft 30. In this type of catheter, the wire guide lumen may extend only from the distal end 4 of the balloon catheter assembly 10 to a point intermediate the distal end 4 and manifold 20 at the proximal end of the catheter shaft 30. The shorter guide wire lumen 226 facilitates the exchange a first balloon catheter assembly 10 for other medical devices, such as a second catheter (e.g., to "exchange out" a balloon catheter, and then "exchange in" a stent-deployment catheter). Referring to FIG. 1, the exchange is preferably executed by leaving a wire guide 50 in place during removal of the first catheter and using it as a guide for the second catheter. The first catheter is withdrawn or otherwise removed over the wire guide 50, and then a second catheter is introduced over the wire guide.

Referring to FIG. 2B, the third tubular member 222 is preferably integrally joined to the stiffening member 210 and the other tubular members 202, 212 within at least the portion of the catheter shaft 30 distal to the wire guide port 32 by the thermoformable material 36 within the outer sleeve 31. Preferably, the stiffening member 210 is not inserted through a lumen within the catheter shaft, but rather, is integrally formed within the catheter shaft after heat processing of the thermoplastic sleeve to flow around the stiffening member 210 and the tubular members 202, 212, 222 to form a single catheter shaft.

Figure 2C:
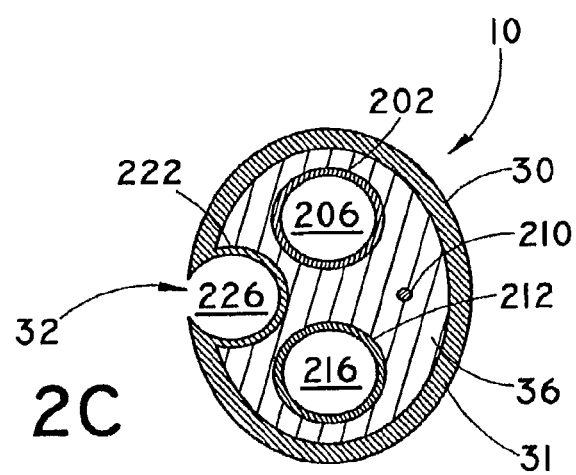
FIG. 2C is a transverse cross-sectional view of along line 2C-2C of the balloon catheter assembly shown in FIG. 1.

FIG. 2C is a third transverse cross-sectional view of the catheter shaft 10 along line C-C', positioned longitudinally distal to line B-B' at the wire guide port 32. In order to facilitate use of the balloon catheter assembly 10 in a short wire (i.e., "rapid exchange") configuration, a wire guide port 32 is provided at the proximal end 222a of the third tubular member 222. A third tubular member 222 defining a wire guide lumen 226 in communication with the wire guide port 32 is positioned within the catheter shaft 30. A proximal end of the third tubular member 222 may be in communication with the wire guide port 32 and a distal end may be proximate the distal end 4 of the catheter shaft 30. The wire guide port 32 may be formed by skiving an opening through the catheter shaft 30 to allow a wire guide 50 to pass through a portion of the balloon catheter assembly 10. Translating the balloon catheter assembly 10 along a wire guide 50 in this manner may facilitate rapid introduction and/or exchange of the balloon catheter assembly 10 along the wire guide 50. The third tubular member 222 is positioned beside the first tubular member 202, the second tubular member 212 and stiffening member 210 described above. Preferably, the third tubular member 222 is adapted to slidably receive a wire guide through the wire guide port 32. In an "over the wire" system, the proximal end of the third tubular member 222 may be in communication with the wire guide port 32 disposed proximate the proximal end 2 of the catheter shaft 30, while the distal end of the third tubular member 222 may be proximate the distal end 4 of the catheter shaft 30.

Referring to FIG. 2C, the third tubular member 222 may be formed from a material having sufficient durability and a desirably low amount of friction. The wall of the third tubular member 222 will also preferably have sufficient structural strength and/or rigidity to prevent the wires of the wire guide 50 from protruding through the wall of the third tubular member 222. For example, the third tubular member 222 may be formed from PTFE having a thickness of about 0.033 mm (0.0013-inches) and an inner diameter of about 0.46 mm (0.018-inches) inner diameter to receive the wire guide. The third tubular member 222 may be adapted to bind to a thermoformable material 36 within the catheter shaft 30, for example by roughening the outer surface of the material. The stiffening member 210 in FIG. 2C may have a smaller cross-sectional area than in FIG. 2B, due to tapering of the stiffening member 210 in the distal direction. The third tubular member 222 may be formed of a lubricious material. Lubricious inner liners for sheaths are well known in the medical arts, and those skilled in the art can readily select an appropriate liner for a particular use. The lubricous material provides a slippery inner surface for easy translation of a wire guide 50 through the wire guide lumen 226 extending longitudinally through the interior of third tubular member 222.

Preferably, the radially outer surface of one or more of the tubular members 202, 212, 222 is roughened in any conventional manner, such as by chemical etching, to form a rough outer surface to facilitate bonding with a dual-lumen thermoplastic sleeve and/or a heat-shrinkable (thermoset) outer sleeve 31 as described above.

In one example, the third tubular member 222 may be incorporated into the balloon catheter assembly 10 by placing the third tubular member 222 adjacent to and along side the dual-lumen thermoplastic "figure 8" sleeve formed from a thermoformable material 36 enclosing the first tubular member 202 and the second tubular 212, described above. The third tubular member 222 may be placed with its proximal end 222a overlapping with the distal end of the tapered stiffening member 210 within the outer heat-shrinkable sleeve. Upon heating the assembly, the thermoplastic sleeve and the outer heat shrinkable sleeve join the first tubular member 202, the second tubular member 212, the third tubular member 222 and the stiffening member 210 together to form the catheter shaft 30. The wire guide port 32 may be formed by cutting away an aperture in the outer sleeve 31 to access the proximal end 222a of the wire guide lumen 226 within the third tubular member 222. The distal end 222b of the wire guide lumen 226 may form the distal end 4 of the catheter shaft 30.

Figure 2D:
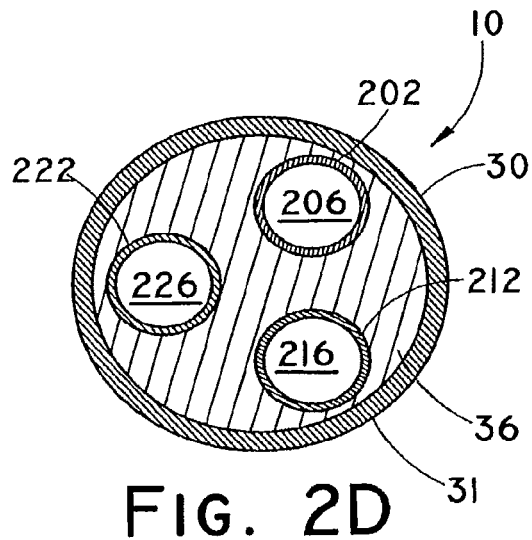
FIG. 2D is a transverse cross-sectional view of along line 2D-2D of the balloon catheter assembly shown in FIG. 1.

FIG. 2D is a fourth transverse cross-sectional view of the catheter shaft 10 along line D-D', longitudinally distal to line C-C' between the wire guide port 32 and the distal region 300 of the balloon catheter assembly 10. The catheter shaft 30 encloses the first tubular member 202, the second tubular member 212 and the third tubular member 222 defining the inflation lumen 206, the fluid delivery lumen 216 and the wire guide lumen 226 (respectively) in a side-by-side orientation. The distal end of the stiffening member 210 is also shown, which preferably extends from the manifold 20 to a distal end positioned distal (e.g., 5 cm) to the wire guide port 32.

Figure 2E:
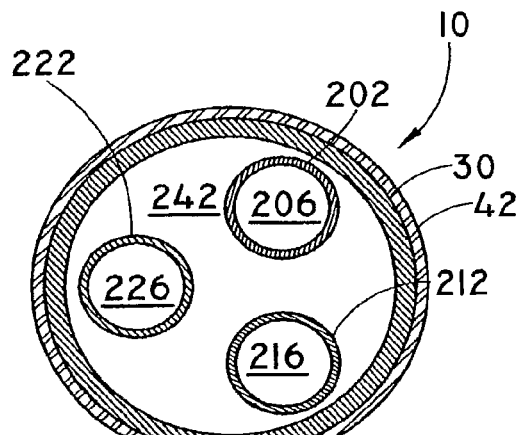
FIG. 2E is a transverse cross-sectional view of along line 2E-2E of the balloon catheter assembly shown in FIG. 1.

FIG. 2E is a fifth transverse cross-sectional view showing the distal region 300 of the balloon catheter assembly 10 along the catheter shaft 30 at line E-E', longitudinally distal to line D-D', at the distal end 212b of the second tubular member 212. The outer balloon 42 defines an annular balloon fluid delivery lumen 242 extending radially between the outer balloon 42 and the inner balloon 44, and extending longitudinally from a proximal seal 242a to a distal seal 242b. The outer balloon 42 is sealed at the proximal seal 242a around the catheter shaft 30, enclosing the first tubular member 202, the second tubular member 212 and the third tubular member 222. The proximal seal 242a may be positioned proximal to the distal end 212b of the second tubular member 212 and is in fluid communication with the fluid delivery lumen 216. The first tubular member 202 enclosing the inflation lumen 206 and the third tubular member 222 enclosing the wire guide lumen 226 preferably remain in side-by-side orientation enclosed by the outer balloon 42.

Figure 2F:
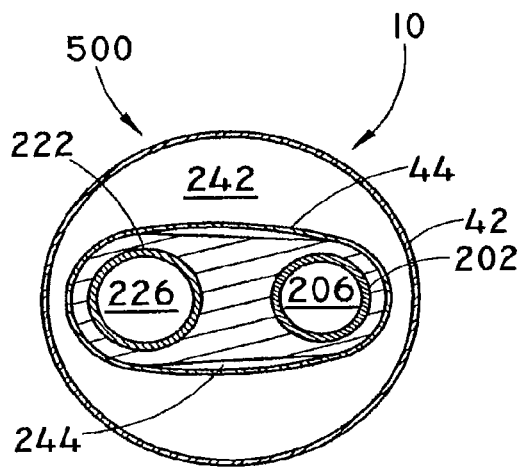
FIG. 2F is a transverse cross-sectional view of along line 2F-2F of the balloon catheter assembly shown in FIG. 1.

FIG. 2F is a sixth cross-sectional view showing the distal region 300 of the balloon catheter assembly 10 along line F-F', longitudinally distal to line E-E', at the distal end 202b of the first tubular member 202. The inner balloon 44 defines a balloon inflation lumen 244 extending radially around the third tubular member 222 passing therethrough, and extending longitudinally from a proximal seal 244a to a distal seal 244b. The inner balloon 44 is sealed at the proximal seal 244a around the first tubular member 202 and the third tubular member 222. The proximal seal 244a is positioned proximal to the distal end 202b of the first tubular member 202 and is in fluid communication with the inflation lumen 206. The annular balloon fluid delivery lumen 242 is shown between the outer balloon 42 and the inner balloon 44.

Figure 2G:
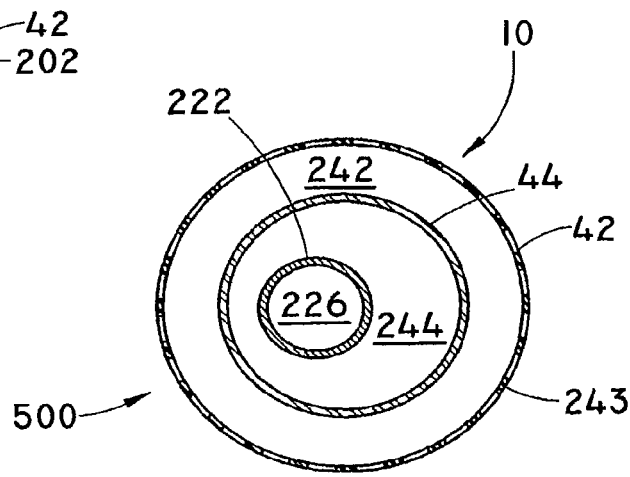
FIG. 2G is a transverse cross-sectional view of along line 2G-2G of the balloon catheter assembly shown in FIG. 1.

FIG. 2G is a seventh cross-sectional view showing the distal region 300 of the balloon catheter assembly 10 along line G-G', longitudinally distal to line F-F', positioned between a proximal seal 244a and a distal seal 244b of the inner balloon 44. The outer balloon 42 is coaxially disposed around the inner balloon 44, defining the balloon fluid delivery lumen 242 in communication with the fluid delivery lumen 216. The inner balloon 44 defines the balloon inflation lumen 244 in communication with the inflation lumen 206 and separated from the wire guide lumen 226 by the third tubular member 222. The outer balloon 42 includes a plurality of apertures 243.

Figure 3A:
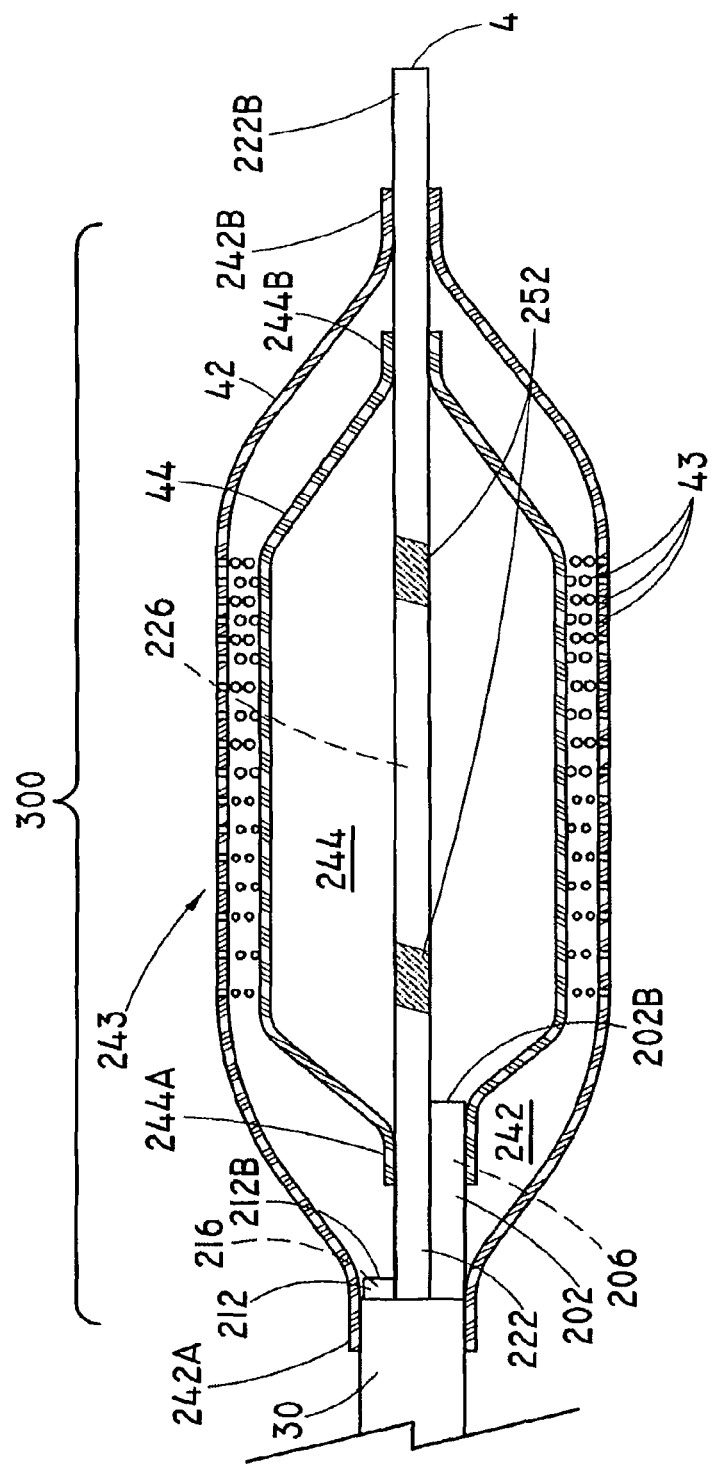
FIG. 3A is a longitudinal cross sectional view of the distal portion of a balloon catheter assembly having multiple balloons.

FIG. 3A is a longitudinal cross-sectional view of the distal region 300 of the balloon catheter assembly 10. The catheter shaft 30 encloses the first tubular member 202, the second tubular member 212 and the third tubular member 222 in a side-by-side configuration. The proximal seal 242a joins the outer balloon 42 to the catheter shaft 30 proximal to the distal end 212b of the second tubular member 212 and the proximal seal 244a of the inner balloon 44. The outer balloon 42 is disposed circumferentially around the inner balloon 44, defining the balloon fluid delivery lumen 242 extends longitudinally from the proximal seal 242a to the distal seal 242b around the third tubular member 222. An inner balloon 44 proximal seal 244a joins the inner balloon 44 around both the first tubular member 202 and the third tubular member 222, proximal to the distal end 202b of the first tubular member 202. The inner balloon 44 is disposed circumferentially around the third tubular member 222 and defines the balloon inflation lumen 244 extending longitudinally from the proximal seal 244a to the distal seal 244b around the third tubular member 222. Preferably, the distal seal 242b may overlap or be positioned around the distal seal 244b. Alternatively, the distal seal 244b of the inner balloon 44 is positioned proximal to the distal seal 242b of the outer balloon 42. Optionally, additional thermoformable material may be placed between the distal end 202b of the first tubular member 202 and the third tubular member 222.

The inner balloon 44 and the outer balloon 42 may be formed from a semi-compliant expandable material. Preferably, the inner balloon 44 and the outer balloon 42 are formed from the materials having a similar Young's modulus and expandability. For example, the balloons may be formed from a polyamide (e.g., nylon 12) material, a polyamide block copolymer (e.g., PEBA) and blends thereof (e.g., nylon 12/PEBA and PEBA/PEBA blends). Alternative materials include polyolefins, polyolefin copolymers and blends thereof; polyesters (e.g., poly(ethylene terephthalate), PET); polyurethane copolymers with MDI, HMDI or TDI hard segment and aliphatic polyester, polyether or polycarbonate soft segment (e.g., Pellethane, Estane or Bionate); and polyester copolymers with 4GT (PBT) hard segment and aliphatic polyester or polyether soft segments (e.g., Hytrel, Pelprene or Arnitel).

The proximal seal and distal seal of each balloon (242a, 242b, 244a, 244b) may be formed in any suitable manner. Typically, the proximal and distal inner surfaces of the balloons 42, 44 are sealably attached to the catheter shaft 30 or a tubular member, as described above. Means of sealing the balloons 42, 44 include, for example, heat sealing, using an adhesive to form the seal, forced convection heating, radio frequency heating, ultrasonic welding, and laser bonding. Shrink tubing may be used as a manufacturing aid to compress and fuse the balloon 42, 44 to the catheter shaft 30 or a tubular member 202, 212, 222. The shrink tubing may be removed and disposed of after the balloon 42, 44 is sealed, or may remain on as part of the connected structure. If the catheter shaft 30 has an outer coating, the balloon 42, 44 may be bonded to the coating or directly to the catheter shaft 30.

When configured for use in a peripheral blood vessel, the inflated diameter of the outer balloon 42 may be about 1.5 mm (0.059-inches) to about 8 mm (0.3-inches), while a catheter intended for coronary vascular applications preferably has an expandable portion 14 with an inflated diameter range of from about 1.5 mm (0.059-inches) to about 4 mm (0.2 inches). When configured for use in bile ducts, the expanded diameter of the outer balloon 42 may be about 5-15 mm (0.2-0.59-inches) with a length of approximately 15-60 mm (0.59-2.4 inches), and the outer diameter of the catheter shaft 30 may be up to about 3.5 mm (0.14-inches). The catheter shaft may be about 3-12 French between proximal to the balloons (i.e., an outer diameter of about 1 mm-4 mm (0.04-0.16-inches)), and preferably about 4-8 French.

Optionally, the balloon catheter assembly 10 may include radiopaque material to provide a means for locating the balloon catheter assembly 10 within a body vessel. For example, the third tubular member 222 may include one or more marker bands 252 annularly disposed around the outside of the third tubular member 222 within the inner balloon 44. If desired, radiopaque bands 252 may be added to the third tubular member 222. Radiopaque marker bands 252 may be used by a clinician to fluoroscopically view and locate the distal portion 300 of the balloon catheter assembly 10 at a treatment site within a body vessel. Various configurations of radiopaque marker bands 252 may be used. For example, radiopaque marker band 252 may be located on a distal end 4 and/or on the third tubular member 222 within the inner balloon 44. As shown, the radiopaque marker bands 252 may be stripes. Such radiopaque markers may be constructed by encapsulating a radiopaque material, such as a metallic ring, within the material of catheter shaft. Alternatively a portion of the catheter shaft may be made radiopaque for example by constructing the portion from a radiopaque polymer. For example a polymer may be mixed with a radiopaque filler such as barium sulfate, bismuth trioxide, bismuth subcarbonate or tungsten. The radiopaque material can comprise any suitable opacifying agent, further including bismuth, tantalum, or other suitable agents known in the art. The concentration of the agent in the coating may be selected to be adequately visible under fluoroscopy.

Figure 3B:
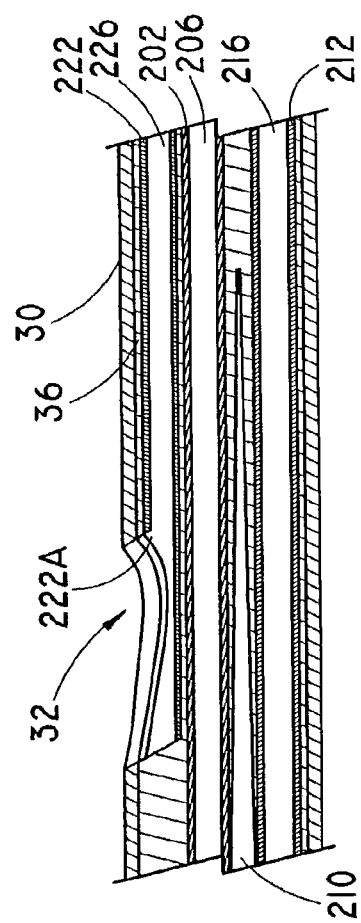
FIG. 3B is a longitudinal cross sectional view of an intermediate portion of a catheter shaft including a wire guide aperture.

FIG. 3B is a longitudinal cross-sectional view of the intermediate region 400 of the balloon catheter assembly 10. The wire guide port 32 may be in communication with the proximal end 222a of the third tubular member 222. The catheter shaft 30 may enclose the first tubular member 202 and the second tubular member 212 in a side-by-side orientation. Optionally, a portion of the catheter shaft 30 can have the first tubular member 202 and the second tubular member 212 in a coaxial configuration, and another portion can have the first tubular member 202 and the second tubular member 212 in the side-by-side configuration. The tapered distal end of the stiffening member 210 may be incorporated substantially parallel to the catheter shaft 30 and outside of the first tubular member 202 and the second tubular member 212. The third tubular member 222 may extend distally from the wire guide port 32, to form a side-by-side orientation with respect to the first tubular member 202 and the second tubular member 212.

Figure 4:
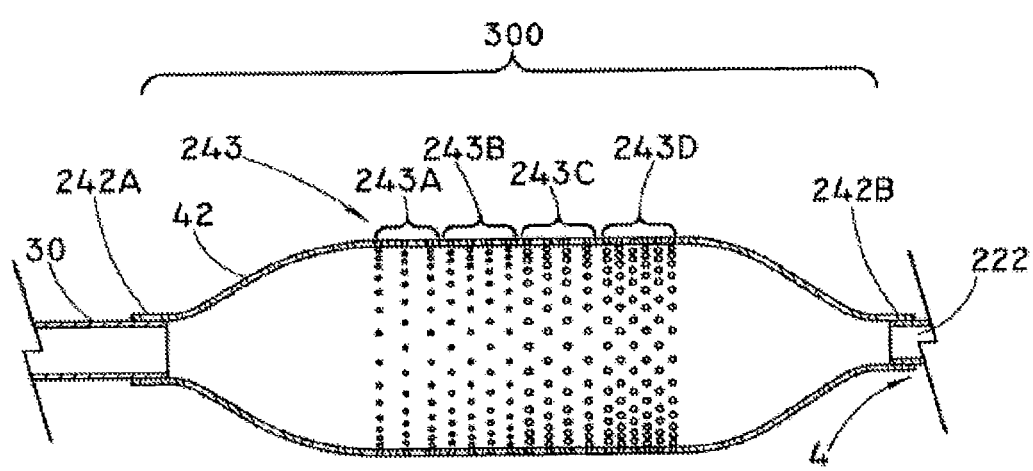
FIG. 4 is detailed view of a plurality of apertures in the outer balloon surface of the distal portion of the balloon catheter assembly shown in FIG. 2.

The outer balloon 42 may include a means for releasing a therapeutic agent from the balloon fluid delivery lumen 242. For example, the outer balloon 42 may define a plurality of openings in communication with the balloon fluid delivery lumen 242. FIG. 4 shows a side view of the distal region 300 of the balloon catheter assembly 10, including the proximal seal 242a of the inflated outer balloon 42 to the catheter shaft 30 and the distal seal 242b of the outer balloon 42 to the third tubular member 222. The outer balloon 42 defines a plurality of apertures 243 that can be disposed along a longitudinal portion of the outer balloon 42. Typically, as the inner balloon 44 inflates, the volume of the annular balloon fluid delivery lumen 242 decreases, increasing the resistance to fluid passing through the fluid delivery lumen 216. To reduce resistance to fluid delivery through the aperture means, the plurality of apertures 243 have a cross sectional area that increases in the distal longitudinal direction along the outer balloon 42. This provides decreased resistance to the release of the therapeutic agent moving distally along the outer balloon 42, allowing for release of the therapeutic agent from the balloon fluid delivery lumen 242 at lower pressures at the injection port 24. The increasing cross sectional area may be provided by increasing the size and/or frequency of the apertures 243 moving distally along the outer balloon 42. For example, the apertures 243 may be configured in a series of regions 243a, 243b, 243c and 243d along the distal longitudinal direction across the outer balloon 42. The second region 243b includes a higher density of apertures than the first region 243a; the apertures in the third region 243c are larger than the apertures in the first region 243a or the second region 243b; and the fourth region 243d has the largest apertures and the highest number of apertures. Accordingly, the cross sectional area of the plurality of apertures 243 increases in the distal direction along the outer balloon 42. The apertures 243 may have any size and shape suitable to provide a desired rate of fluid release from the balloon fluid delivery lumen 242. Typically, the apertures 243 may have any suitable size and shape, but preferably have at least one dimension between about 10 micrometer (0.0004 inch) to about 1 mm (0.04 inch). The apertures 243 may be formed by any suitable method including mechanical punching, laser cutting, and the like.

FIG. 5A is a cut-away longitudinal cross section of the proximal end of the balloon catheter assembly 10. The proximal end 212a of the second tubular member 212 may be aligned with the proximal end 36a of the "figure-8" thermoformable material 36, while the first tubular member 202 defining the inflation lumen 206 extends out of the thermoformable material 36 in the proximal direction to a proximal end 202a. A first tubular member extension 202' is fitted around the portion of the inflation lumen, defining a secondary inflation lumen 206' in fluid communication with the inflation lumen 206. The distal end of the first tubular member extension 202' is sealed around the outer portion of the proximal end 202a of the first tubular member 202 extending proximally from the thermoformable material 36. FIG. 5B is a cutaway view of a manifold 20 attached to the catheter balloon catheter assembly 10 showing the manifold 20 joined to the catheter shaft 30 portion shown in FIG. 5A. FIG. 5B shows the proximal end of the catheter assembly 10 shown in FIG. 5A connected to a manifold 20. The proximal end 202a' of the first tubular member extension 202' may be in fluid flow communication with an inflation port so as to continuously connect the inflation port 22 to the inflation lumen 206 through the secondary inflation lumen 206'. A second tubular member extension 33 may be placed around the proximal end 36a of the thermoformable material 36, but inside the outer sleeve 31. The second tubular member extension 33 may define a proximal injection lumen 208 in fluid communication with the fluid delivery lumen 216 and an injection port. Preferably, the proximal end of the tubular member extension 33 is securely fitted to a manifold in a manner providing sealed fluid flow communication between the fluid delivery lumen 216 within the proximal end 212a of the second tubular member 212 and a fluid injection port within a manifold. The proximal injection lumen 208 is preferably separated from the inflation lumen 206 and the secondary inflation lumen 206'. The proximal end of the stiffening member 210 may be positioned within the proximal injection lumen 208, or terminate within a manifold. The stiffening member 210 is preferably attached to the thermoformable material 36 by heat processing the thermoformable material 36 around the stiffening member with a proximal portion of the stiffening member extending in the proximal direction from the thermoformable material 36. An injection port 24 is joined to the proximal injection lumen 208 in communication with the fluid delivery lumen 216. The proximal end 202a' of the first tubular member extension 202' is sealably connected to manifold 20 at the inflation port 22 such that the inflation port 22 is in fluid communication with the secondary inflation lumen 206' and the inflation lumen 206. The proximal end of the stiffening member 210 is also shown.

In another aspect of the first embodiment, fluid delivery catheters having a higher burst pressure for a given outer diameter are provided. In generally, fluid delivery catheters are desirably made small and thin. Accordingly, their structural strength may be limited by the thickness and type of material forming the catheter's walls. The amount of pressure and flow rate that the catheter can support without damage may also be limited. If the maximum pressure the catheter can withstand (the burst pressure) or the maximum flow rate is exceeded, the catheter may be damaged or may completely fail possibly spilling fluids from the catheter into the body. During high pressure injections, escaping fluid may also damage the surrounding tissues. The catheter shaft configurations described provide increased burst pressure without requiring an increase in the diameter of the fluid delivery lumen or the outer diameter of the catheter shaft by including one or more tubular members (e.g., 202, 212) lining lumens extending through the catheter shaft. This permits lower fluid delivery pressures for a given burst pressure, compared to catheter shaft configurations without the tubular members. Exemplary catheter shaft configurations may have an outer diameter of about 1.1 mm (0.042-inches) and a fluid delivery lumen having an inner diameter of about 0.36 mm (0.014-inches), and a burst pressure of about 2.7-35 MPa (27-35 atmospheres) or more. The individual tubular members may be perfluorocarbon liners with a burst pressure of about 1.5 MPa (15 atmospheres) at about 0.25 mm (0.010-inches) to 0.33 mm (0.013-inches) thickness. A fluid delivery catheter for medical procedures may include a shaft portion having a distal end insertable into a body lumen, the shaft portion including a wall defining a fluid delivery lumen extending therewithin and a first tubular member coupled to the wall to increase a burst pressure of the shaft portion, wherein the first liner cooperates with a material of the wall to define a flexible region of the shaft portion allowing the shaft portion to be atraumatically inserted into the body lumen.

In one particular aspect, an intraluminal drug delivery catheter assembly may include a means for expandably contacting the balloon with the wall of a body vessel (e.g., one or more balloons) and/or a means for delivering a therapeutic agent through the catheter shaft (e.g., a plurality of apertures in the balloon). The catheter shaft may extend from a proximal end to a distal end and define an inflation lumen spaced from a fluid delivery lumen. The catheter shaft may be formed in part by a thermoformable polymer and include a stiffening member within a portion of the catheter shaft in non-translatable contact with the thermoformable polymer. The catheter assembly may include a balloon comprising a plurality of apertures mounted around at least a portion of the distal end of the catheter shaft, with at least a portion of the plurality of apertures having a total cross sectional area that increases in a distal direction along the second balloon.

In another particular aspect, the catheter assembly may include an outer sleeve enclosing a thermoformable material and one or more fluid delivery lumens lines with a liner material such that the burst pressure of the catheter assembly is greater than the burst pressure of the thermoformable material, the outer sleeve and the liner material independent of one another. Methods of increasing the burst pressure of a catheter shaft may include providing a fluorinated carbon liner and an outer sleeve, as described herein, to a conventional catheter shaft formed from a thermoformable material.

In another embodiment, methods of delivering a therapeutic agent to a body vessel are provided. Preferably, the methods include the step of inserting into a body vessel a therapeutic agent delivery balloon catheter assembly over a wire guide. The balloon catheter assembly may include any balloon catheter assembly disclosed herein. For example, the balloon catheter assembly may include: (1) a catheter shaft extending from a proximal end to a distal end and including one or more tubular members that may define an inflation lumen adjacently spaced from a fluid delivery lumen and/or a wire guide lumen, the catheter shaft formed in part by a thermoformable polymer; (2) a deflated first balloon mounted on the distal end of the catheter shaft in communication with the inflation lumen; (3) a deflated second balloon mounted around at least a portion of the first balloon on the distal end of the catheter shaft in communication with the fluid delivery lumen, defining an annular balloon fluid delivery lumen between the first balloon and the second balloon. The second balloon preferably includes a plurality of apertures in the second balloon in communication with the balloon fluid delivery lumen, the plurality of apertures having a total cross sectional area that increases in a distal direction along the second balloon. The catheter shaft preferably includes a stiffening member within a portion of the catheter shaft in non-translatable contact with the thermoformable polymer. The balloon catheter assembly may be translated through the body vessel over a wire guide slidably extending through the wire guide lumen to a point of treatment. The first balloon may be inflated at the point of treatment to place the second balloon in contact with the wall of the body vessel.

A therapeutic agent may be delivered through the fluid delivery lumen at a pressure effective to deliver the therapeutic agent to the wall of the body vessel through the plurality of apertures in the second balloon. The therapeutic agent may be delivered by direct local administration to the vessel site or injury through the plurality of apertures in the second balloon. The antisense compound may have: (i) morpholino subunits linked together by phosphorodiamidate linkages, 2 atoms long, joining the morpholino nitrogen of one subunit to the 5' exocyclic carbon of an adjacent subunit; and (ii) a sequence of bases attached to the subunits and containing a therapeutically beneficial antisense nucleotide sequence. While the compound need not necessarily 100% complementary to the target sequence, it is preferably effective to stably and specifically bind to the target sequence such that expression of the target sequence is modulated. The appropriate length of the oligomer to allow stable, effective binding combined with good specificity is about 8 to 40 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target is maintained. The compound preferably contains internal 3-base triplet complementary to the AUG site, and bases complementary to one or more bases 5' and 3' to the start site. One preferred compound sequence is the 20 mer having the base sequence: 5'-ACG TTG AGG GGC ATC GTC GC-3', where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions. Preferably, the therapeutic agent is a morpholino antisense compound having (i) from 8 to 40 nucleotides, including a targeting base sequence that is complementary to a region that spans the translational start codon of a c-myc mRNA; and (ii) uncharged, phosphorous-containing intersubunit linkages, in an amount effective to reduce the risk or severity of restenosis in the patient. These therapeutic agents are described in U.S. Pat. No. 7,094,765 and published US patent application US 2006/0269587 A1, which are incorporated herein by reference in their entirety. While the therapeutic agent is described with respect to certain preferred antisense compounds, any suitable therapeutic agent in fluid form (i.e., a gas and/or a liquid) or in a fluid carrier may be delivered from the balloon catheter assembly.

The balloon catheter assembly 10 shown in the figures herein is one preferred embodiment of the invention that includes a dual balloon assembly at the distal end of the catheter shaft 30. Other embodiments preferably include a catheter shaft extending from a proximal end to a distal end and defining an inflation lumen spaced from a fluid delivery lumen, the catheter shaft formed in part by a thermoformable polymer. The catheter shaft may include one or more balloons comprising a plurality of apertures mounted around at least a portion of the distal end of the catheter shaft, a means for delivering a therapeutic agent through the catheter shaft through the plurality of apertures in the balloon and/or a means for expandably contacting the balloon containing the apertures with the wall of a body vessel. In the embodiment described with respect to the figures above, the means for delivering a therapeutic agent is exemplified as a fluid delivery lumen defined by a second tubular member 212. Alternative structures may be substituted as a means for delivering the therapeutic agent through the catheter shaft, such as a lumen formed within the thermoformable material 36 without the tubular member 212, or a lumen formed in a second catheter shaft or a second tube adhered to the outside of the catheter shaft 30. Alternative structures may also be substituted as a means for expandably contacting the balloon with the wall of a body vessel, which is exemplified in the figures as including an inner balloon 44. For example, a single balloon containing apertures or a microporous membrane may be used as the perforated balloon and the means for contacting the balloon. Alternatively, an expandable frame or other mechanical means may be used to contact a perforated balloon with the body vessel. Other single balloon embodiments are described below.

EXAMPLES

Example 1

Manufacturing a Balloon Catheter Therapeutic Agent Delivery Assembly

Figure 6E:
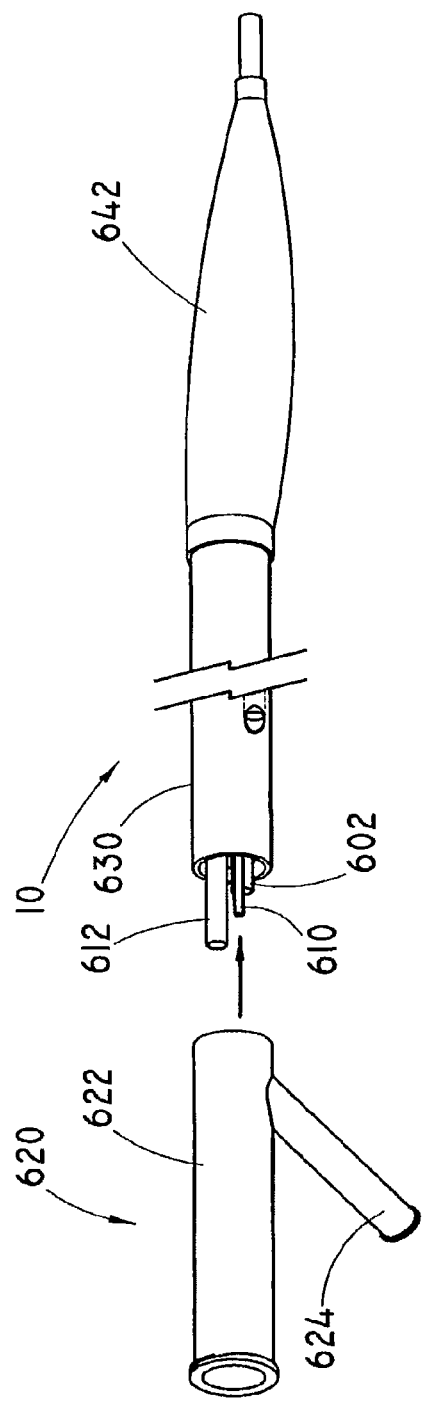
FIG. 6E is a fifth exploded view of a portion of a balloon catheter assembly.

An exemplary method of making the balloon catheter assembly 10 is described with reference to FIGS. 6A-6E. Those of skill will appreciate that this and other embodiments may be constructed using alternative methods within the scope of the present invention. FIG. 6A is a first exploded view of the catheter assembly 10. A coextruded PEBA thermoplastic sleeve 634 can have a "figure-8" transverse cross section defining a pair of parallel longitudinal lumens with a wall of about 0.64 mm (0.0025-inches) between the lumens. A first poly(tetrafluoroethylene) (PTFE) tubular member 602 can be placed 661 within the first lumen of the thermoplastic sleeve 634. A second PTFE tubular member 612 can be separately placed 662 within the second lumen of the thermoplastic sleeve 634. A third PTFE tubular member 626 can be placed 663 outside of the thermoplastic sleeve 634, adjacent to and substantially parallel with the thermoplastic sleeve 634. A stiffening member 610 may also be placed 664 outside of the thermoplastic sleeve 634, adjacent to and substantially parallel with both the third PTFE tubular member 626 and the thermoplastic sleeve 634. The catheter assembly 10 may include one or more tubular members, the stiffening member, or any combination thereof.

As shown in FIG. 6B, the first tubular member 602 can extend both proximally and distally from the thermoplastic sleeve 634. The second PTFE tubular member 612 can be placed within the second lumen of the thermoplastic sleeve 634 and can extend distally therefrom to a position between the distal end of the thermoplastic sleeve 634 and the distal end of the first tubular member 602. The first tubular member 602 and the second tubular member 612 may each have an inner diameter of about 0.36 mm (0.014-inches). The third tubular member 626 can extend from a proximal end positioned between the proximal and distal ends of the thermoplastic sleeve 634 and to a distal end positioned distal to both the distal end of the first tubular member 602 and the distal end of the second tubular member 612. The distal ends of the three tubular members 602, 612, 626 each can extend from the distal end of the thermoplastic sleeve 634 and can be distally staggered with respect to one another with the third tubular member 626 extending farthest from the distal end of the thermoplastic sleeve 634, followed by the distal end of the first tubular member 602 and the distal end of the second tubular member 612, respectively. A tapered 304 stainless steel wire stiffening member 610 may also be placed along adjacent to the distal end of the thermoplastic sleeve 634 and along a proximal portion of the third tubular member 626. The stiffening member 610 may have a diameter of about 0.38 mm (0.015-inches) at the proximal end and about 0.05 mm (0.002-inches) at the distal tip. An outer sleeve 630 is placed 665 around the thermoplastic sleeve 634, tubular members 602, 612, 626 and the stiffening member 610. A wire guide port 632 can be formed by skiving an opening through the outer sleeve 630 to allow a wire guide to pass through the third tubular member 626 of the balloon catheter assembly 10. One or more marker bands 652 may be annularly disposed around the outside of the third tubular member 652, or otherwise provided such as disclosed herein.

Referring to FIG. 6C, an inner balloon 644 is formed by heat sealing a first non-porous expandable nylon 12 sheet around the distal end of both the first tubular member 602 and the third tubular member 626 to form a proximal seal, and heat sealing the distal end of the first sheet around the third tubular member 626. The distal end of the first tubular member 602 is positioned within the inner balloon 644 and is in communication with an inflation lumen within the first tubular member 602.

Referring to FIG. 6D, a perforate outer balloon 642 is formed by heat sealing a second porous expandable nylon 12 sheet around the distal end of the catheter outer sleeve 630, including tubular members 602, 612, 626, and heat sealing the distal end of the second sheet around the third tubular member 626 distal to the distal heat seal of the inner balloon 644. The perforations in the second sheet may be formed prior to or after attaching the sheet to the catheter to form the outer balloon 642. An annular lumen 643 is defined between the outer balloon 642 and the inner balloon 644. The distal end of the second tubular member 612 is positioned within the annular lumen 643 between the outer balloon 642 and the inner balloon 644 and is in communication with a fluid delivery lumen within the second tubular member 612. Referring to FIG. 6E, a manifold 620 may be joined to the proximal end of the catheter assembly shown in FIG. 6D such that the inflation port 622 is in fluid flow communication with the first tubular member 602 and the injection port 624 is in separate fluid flow communication with the second tubular member 612.

Example 2

Catheter Shaft Burst Pressure Measurements

Catheter shaft burst pressure was measured. One end of the shaft to be measured was closed off and the interior of the shaft was pressurized with a measurable source, until a discontinuity or fault (such as a hole) developed in the shaft. The pressure was measured in atmospheres (atm) using a burst tester such as a PT-3070 Burst Tester (Laguna Niguel, Calif.). Each component was pressurized in 1 atm (0.1 MPa) increments using a pressurization rate of 0.40 ml/s starting at 1 atm (0.1 MPa) and held at each pressure for three seconds. A failure was defined as a drop in pressure of 1.50 atm (0.15 MPa) or greater during the three second hold. Four separate burst pressures were measured for each of three component portions of the catheters: a perfluorocarbon liner (202, 212, 222), a thermoformable "figure 8"-shaped tubing having an inner diameter of 0.0215-inches (0.546 mm) with a wall of 0.0025-inches (0.064 mm) (36), and a PEBAX heat-shrink outer liner (31). The burst data for each sample is shown in Table 1. The liners burst at about 19-20 atmospheres (1.9-2 MPa), at which pressure fluid could no longer be contained within the liners. The thermoformable tubing and outer liners burst at lower pressures.

TABLE 1

| | Burst Pressure (atm (MPa)) | | | |
| --- | --- | --- | --- | --- |
| | Sample 1 | Sample 2 | Sample 3 | Sample 4 |
| 0.015 in.(0.38 mm) ID TFE Liner Burst pressure | 19.05 (1.930) | 19.10 (1.935) | 19.03 (1.928) | 20.14 (2.041) |
| Figure "8" Material Burst pressure | 10.04 (1.017) | 9.04 (0.916) | 9.01 (0.913) | 9.02 (0.914) |
| PEBAX heat-shrink outer liner burst pressure | 15.09 (1.529) | 18.03 (1.827) | 14.68 (1.487) | 20.12 (2.039) |

Figure 7:
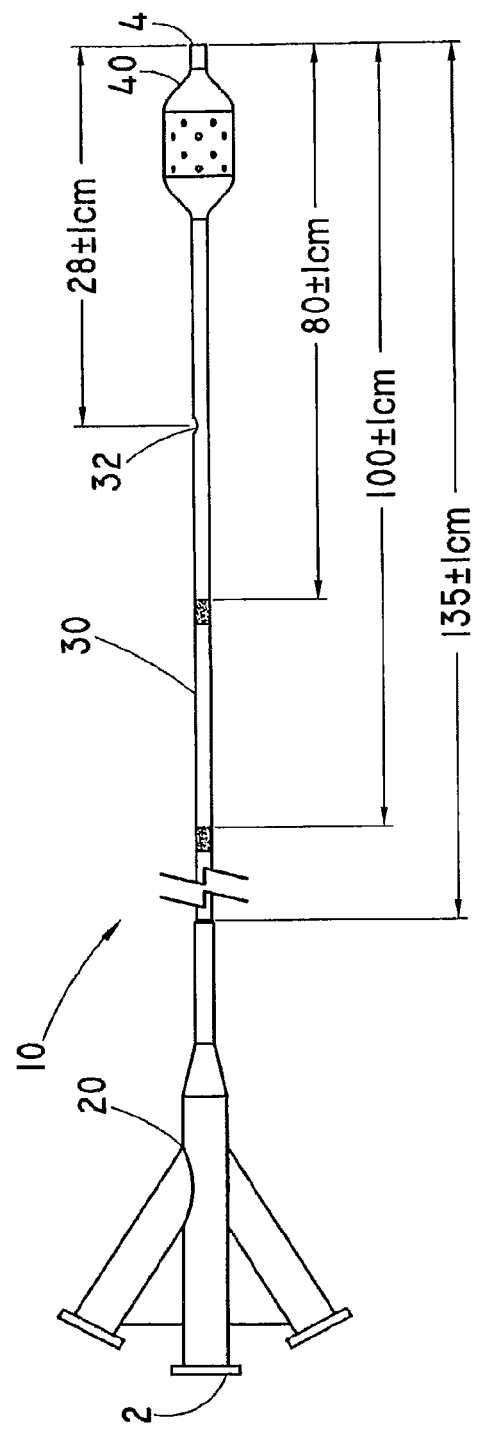
FIG. 7 is a perspective view of a particular example of a balloon catheter assembly.

Next, the burst pressure of a catheter assembly (10) as shown in FIG. 7 was measured for five identical catheter assemblies each including three perfluorocarbon liners (202, 212, 222), a thermoformable "figure 8"-shaped tubing having an original inner diameter of 0.0215-inches (0.546 mm) with a wall of 0.0025-inches (0.064 mm) (36), and a PEBAX heat-shrink outer liner (31) having an inner diameter of 0.041-inches (1.0 mm) and a wall thickness of about 0.0030-inches (0.076 mm). The assembly was heated and the thermoformable "figure 8" material flowed around the three perfluorocarbon liners, as well as a stiffening member. The outer diameter of the catheter shaft (30) was about 0.04-inches (1 mm) (e.g., about 0.047-inches (1.2 mm), or about 3-4 French).

The balloon catheter assemblies (10) were constructed according to the preferred embodiment of Example 1. The burst data for each sample is shown in Table 2.

TABLE 2

| | Burst Pressure (atm (MPa)) | | | | |
|---|---|---|---|---|---|
| | Sample 1 | Sample 2 | Sample 3 | Sample 4 | Sample 5 |
| Composite shaft burst pressure | 29.22 (2.961) | 29.18 (2.957) | 35.30 (3.577) | 27.16 (2.752) | 31.19 (3.160) |

Notably, the burst pressures of the catheter assemblies (10) were each at least about 30 atmosphere (3 MPa) (27-35 atmospheres (2.7-3.5 MPa)), while the individual liners tested above burst at a lower pressure of about 20 atmospheres (2 MPa). Therefore, while fluid above 20 atmospheres (2 MPa) could not be contained by any one of the liners, thermoformable material or outer sleeve individually, pressures of at least about 30 atmospheres (3 MPa) could be conducted along the catheter shaft assemblies of Example 1.

FIG. 8 illustrates a single balloon catheter assembly 10' with the above described constructed catheter shaft 30, including an "over the wire" system, although a "short wire" system may still be used. The catheter shaft 30 may include one or more tubular members defining at least one of the inflation lumen, the fluid delivery lumen, and the wire guide lumen. The stiffening member, as described above, may also be included in the catheter shaft 30. The "over the wire" system has the wire guide port 32 positioned as part of the manifold 20, and may include the inflation port 22 and the injection port 24. The distal region 300 of the balloon catheter assembly 10' includes an inflation balloon 44'. The balloon 44' is preferably non-porous and in fluid communication with the inflation port 22 through the body of the catheter shaft 30. A means 60 for delivering the therapeutic agent from the injection port 24 may be included in the catheter shaft 30. The means 60 for delivering the therapeutic agent to the body vessel may include a side port in fluid communication with the fluid delivery lumen or a plurality of apertures in the balloon. The side port can be disposed in the distal longitudinal direction of the balloon 44' (as shown in FIG. 8) proximate the distal end 4 of the catheter shaft 30, or optionally may be disposed in the proximal longitudinal direction of the balloon 44', where the location is spaced a shorter distance from the balloon 44' than from the proximal end 2 of the catheter shaft 30. The balloon 44' may be sealed to the distal end 4 of the catheter shaft 30, within the distal portion 300 of the catheter shaft 30 housing the distal portion of the wire guide lumen. The balloon catheter assembly 10' may be translated over the wire guide 50 shown extending from the wire guide port 32, through the catheter shaft 30 and extending from the distal end 4 of the catheter shaft 30. In another embodiment, the single balloon catheter assembly 10' may be a microcatheter having a diameter of about 0.36 mm (0.014 inches) with the catheter shaft less than about 0.97 mm (0.038 inches). Embolic particles may be inserted through the lumen of one of the tubular members, before or after removal of the wire guide, and delivered into the body vessel distal to the balloon, which functions as an occlusion balloon to prevent particles from flowing to unintended or undesirable regions.

Those of skill in the art will appreciate that other embodiments and variants of the structures and methods described above may be practiced within the scope of the present invention. It is therefore intended that the foregoing detailed description be regarded as illustrative rather than limiting, and that it be understood that it is the following claims, including all equivalents, that are intended to define the spirit and scope of this invention.

We claim:

1. A method for making a balloon catheter, comprising:
(a) forming a catheter shaft, said forming including:
disposing a first fluorinated hydrocarbon tube in a first lumen of a thermoplastic polymer sleeve material, the first fluorinated hydrocarbon tube having a melting point higher than that of the thermoplastic polymer sleeve material;
disposing a second fluorinated hydrocarbon tube in a second lumen of the thermoplastic polymer sleeve material, the second fluorinated hydrocarbon tube having a melting point higher than that of the thermoplastic polymer sleeve material;
heating the thermoplastic polymer sleeve material, with the first and second fluorinated hydrocarbon tubes disposed in the first and second lumens, to provide a heated catheter shaft assembly in which the thermoplastic polymer sleeve material is molten; and
compressing the heated catheter shaft assembly so as to cause the molten thermoplastic polymer sleeve material to flow around and join together the first fluorinated hydrocarbon tube and the second fluorinated hydrocarbon tube; and
(b) mounting a balloon on the catheter shaft with an interior of the balloon in fluid communication with a lumen defined by the first fluorinated hydrocarbon tube.

2. The method of claim 1, wherein said thermoplastic polymer is comprised of a polyether block amide.

3. The method of claim 1, wherein said first and second fluorinated hydrocarbon tubes are each comprised of a polytetrafluoroethylene tube.

4. The method of claim 1, also comprising disposing heat shrink tubing around said thermoplastic polymer sleeve material, and wherein said heating is also sufficient to shrink the heat shrink tubing so as to cause said compressing.

5. The method of claim 4, wherein said heat shrink tubing is comprised of a polyether block amide.

6. The method of claim 1, wherein said catheter shaft segment has a generally circular cross section upon completion of said heating and compressing.

7. The method of claim 4, also comprising disposing a third fluorinated hydrocarbon tube within said heat shrink tubing prior to said heating.

8. The method of claim 7, wherein said third fluorinated hydrocarbon tube is disposed within the heat shrink tubing between an inner surface of the heat shrink tubing and an outer surface of the thermoplastic sleeve material.

9. The method of claim 4, also comprising disposing a stiffening member within said heat shrink tubing prior to said compressing.

10. The method of claim 9, wherein said stiffening member is a tapered mandrel.

11. The method of claim 1, wherein the first fluorinated hydrocarbon tube and the first lumen are sized such that void space occurs between the first fluorinated hydrocarbon tube and walls defining the first lumen, the second fluorinated hydrocarbon tube and the second lumen are sized such that void space occurs between the second fluorinated hydrocarbon tube and walls defining the second lumen, and compressing the heated catheter shaft assembly causes the molten thermoplastic polymer sleeve material to fill the void space between the first fluorinated hydrocarbon tube and the first lumen and the void space between the second fluorinated hydrocarbon tube and the second lumen.

12. The method of claim 1, also comprising disposing heat shrink tubing around said thermoplastic polymer sleeve material, and wherein said heating is also sufficient to shrink the heat shrink tubing so as to cause said compressing, wherein said heat shrink tubing is subjected to at least partial cross-linking.

13. The method of claim 1, also comprising disposing heat shrink tubing around said thermoplastic polymer sleeve material, and wherein said heating is also sufficient to shrink the heat shrink tubing so as to cause said compressing, wherein said heat shrink tubing comprises FEP.

14. The method of claim 1, wherein at least one of said first and second fluorinated hydrocarbon tubes is comprised of a polyimide tube.

15. The method of claim 1, wherein said balloon is an inner non-porous balloon, and also comprising an outer porous balloon mounted on the catheter shaft with an interior of the outer porous balloon in fluid communication with a lumen defined by the second fluorinated hydrocarbon tube.

16. The method of claim 9, wherein said stiffening member is disposed within the heat shrink tubing between an inner surface of the heat shrink tubing and an outer surface of the thermoplastic sleeve material.

17. The method of claim 1, wherein said thermoplastic polymer sleeve is a dual-lumen thermoplastic FIG. 8 sleeve.

18. The method of claim 8, wherein a lumen defined by said third fluorinated hydrocarbon tube is adapted to be a wire guide lumen and extends from a point intermediate the balloon and a manifold at a proximal end of the catheter shaft to a point distal from the balloon, and cutting away an aperture in the heat shrink tubing to access a proximal end of the wire guide lumen.

19. The method of claim 18, wherein said thermoplastic polymer sleeve is a dual-lumen thermoplastic FIG. 8 sleeve, also comprising disposing a stiffening member within said heat shrink tubing prior to said compressing, wherein said stiffening member is disposed within the heat shrink tubing between an inner surface of the heat shrink tubing and an outer surface of the thermoplastic sleeve material, said stiffening member is a tapered mandrel, and a proximal end of the third fluorinated hydrocarbon tube overlaps a distal end of the tapered mandrel.

20. The method of claim 19, wherein at least one of said first and second fluorinated hydrocarbon tubes is comprised of a polyimide tube, and said balloon is an inner non-porous balloon, and also comprising an outer porous balloon mounted on the catheter shaft with an interior of the outer porous balloon in fluid communication with a lumen defined by the second fluorinated hydrocarbon tube.

* * * * *